(12) United States Patent
Fujii et al.

(10) Patent No.: US 8,974,392 B2
(45) Date of Patent: Mar. 10, 2015

(54) ULTRASONIC PROBE

(75) Inventors: Kiyoshi Fujii, Kanagawa (JP); Akira Shimasaki, Kanagawa (JP); Masahiro Shinkai, Tokyo (JP); Eiichi Ookawa, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 1220 days.

(21) Appl. No.: 12/373,790

(22) PCT Filed: Jul. 19, 2007

(86) PCT No.: PCT/JP2007/064283
§ 371 (c)(1),
(2), (4) Date: Jan. 14, 2009

(87) PCT Pub. No.: WO2008/010558
PCT Pub. Date: Jan. 24, 2008

(65) Prior Publication Data
US 2009/0275836 A1 Nov. 5, 2009

(30) Foreign Application Priority Data

Jul. 20, 2006 (JP) ................... 2006-198763
Sep. 8, 2006 (JP) ................... 2006-244786
Nov. 8, 2006 (JP) ................... 2006-303236
Nov. 8, 2006 (JP) ................... 2006-303237

(51) Int. Cl.
*A61B 8/14* (2006.01)
*A61B 8/13* (2006.01)
(Continued)

(52) U.S. Cl.
CPC ............... *A61B 8/13* (2013.01); *A61B 8/4218* (2013.01); *A61B 8/4281* (2013.01);
(Continued)

(58) Field of Classification Search
CPC .................. A61B 8/12; A61B 8/4281
USPC .......................................... 600/459
See application file for complete search history.

(56) References Cited

U.S. PATENT DOCUMENTS 4,065,976 A 1/1978 Taenzer et al.
4,238,962 A 12/1980 Taenzer
(Continued)

FOREIGN PATENT DOCUMENTS

DE 2924194 B1 10/1980
FR 2868495 A1 10/2005
(Continued)

OTHER PUBLICATIONS

PDF of a dictionary.com definition.*
(Continued)

*Primary Examiner* — Tse Chen
*Assistant Examiner* — Hien Nguyen
(74) *Attorney, Agent, or Firm* — Holtz, Holtz, Goodman & Chick PC

(57) ABSTRACT

An ultrasonic probe has an organism contact portion that is shaped for use along a comparatively large curvature and can easily be used while closely contacting an organism. The probe includes a first cylinder pulley secured to a probe casing, an arm secured to a motor spindle extending through the first pulley, and a second cylinder pulley rotatably arranged on the opposite side and coupled to the first pulley by a wire. The second pulley is equipped with a slider shaft that is arranged to be extendable by a slider bearing. The slider shaft is equipped with a roller contacting a guide rail of the casing. An ultrasonic element is attached to the distal end of the slider shaft to provide the telescopic structure for the slider shaft. In this manner, the size of a scanning mechanism, for oscillating the ultrasonic element along a large curvature, is reduced.

36 Claims, 18 Drawing Sheets

(51) Int. Cl.
*A61B 8/00* (2006.01)
*A61B 8/08* (2006.01)
*G10K 11/35* (2006.01)

(52) U.S. Cl.
CPC ............ *A61B 8/4455* (2013.01); *A61B 8/4461* (2013.01); *A61B 8/4466* (2013.01); *A61B 8/483* (2013.01); *G10K 11/355* (2013.01); *A61B 8/4488* (2013.01)
USPC .......................................................... 600/459

(56) References Cited

U.S. PATENT DOCUMENTS

| | | | |
|---|---|---|---|
| 4,275,597 A | 6/1981 | Quedens et al. | |
| 4,850,362 A | 7/1989 | Rello et al. | |
| 6,023,165 A * | 2/2000 | Damadian et al. | 324/318 |
| 2008/0276736 A1 | 11/2008 | Petetin | |

FOREIGN PATENT DOCUMENTS

| | | |
|---|---|---|
| JP | 58-064308 U | 4/1983 |
| JP | 58-64308 U | 4/1983 |
| JP | 59-042970 U | 3/1984 |
| JP | 59-111110 U | 7/1984 |
| JP | 59-190208 U | 12/1984 |
| JP | 59-020652 B2 | 8/1985 |
| JP | 61-013942 A | 1/1986 |
| JP | 62-12309 U | 1/1987 |
| JP | 62-012309 U | 1/1987 |
| JP | 2-17047 A | 1/1990 |
| JP | 03-184532 A | 8/1991 |
| JP | 3-292939 A | 12/1991 |
| JP | 04-282136 A | 10/1992 |
| JP | 5-23339 A | 2/1993 |
| JP | 06-038962 A | 2/1994 |
| JP | 7-299066 A | 11/1995 |
| JP | 10201762 A | 8/1998 |
| JP | 2004-337476 A | 12/2004 |

OTHER PUBLICATIONS

European Search Report for Application No. 07791036.2-2319/ 2050397 PCT/JP2007064283 dated Jun. 27, 2012.
International Search Report, Jun. 9, 2007.

* cited by examiner

ULTRASONIC PROBE

TECHNICAL FIELD

The present invention relates to an ultrasonic probe used for the transmission and reception of an ultrasonic beam. In particular, the present invention relates to a compact, hand-held ultrasonic probe such that an array type element, which is formed by arranging piezoelectric devices in a strip and performs electrical scanning to obtain tomograms, or a single element, is mechanically swept in parallel, or is oscillated, in a direction perpendicular to the electrical or mechanical scanning direction, so that a three dimensional image can be obtained for the organism. That is, the present invention relates to an appropriate ultrasonic probe for a mechanical scanning system, for which the main purpose is the acquisition of three-dimensional images of the mammary glands, the thyroid, the carotid artery, the superficial blood vessels, and of superficial layer structures (hereinafter called superficial tissues) and the acquisition of a three-dimensional image by scanning the body surface, through a superficial contact area, even when the ribs or the anterior fontanelle is present in between.

BACKGROUND ART

In order to obtain an ultrasonic image of superficial tissue easily and quickly, a broad visual field in the vicinity of the body surface must be obtained using an array type element, or a single element, and a mechanical scanning process that must also be performed along the shape of the body surface, in a direction perpendicular to the scanning direction of the array type element or the single element. A hand-held ultrasonic probe is of great value in reducing expenditures; three-dimensional images of all superficial tissues can be obtained using a single three-dimensional ultrasonic probe, and thus, during a diagnosis, no labor is required for the exchange of probes, and a plurality of three-dimensional ultrasonic probes is not needed. However, for the acquisition of three-dimensional images of the carotid artery and the thyroid, the shape formed for the ultrasonic probe must be as small as possible, because the diagnostic locations where these organs lie immediately below the jaw. Thus, there are conflicting requests, i.e., for increasing the three-dimensional diagnosis area and for downsizing a three-dimensional ultrasonic probe. In addition, since an ultrasonic probe is hand-held, a further request is that the probe be compact and light.

A conventional superficial tissue imaging acquisition method of this type is available, whereby an ultrasonic probe is rotated while a breast applicator is interposed between a breast and the probe, and a tomogram of the overall area of the breast is obtained (see, for example, patent document 1 below).

Further, another method is one whereby an ultrasonic probe is arranged in a water tank and is swept in parallel to obtain a tomogram of an entire breast (see, for example, patent document 2 below). In addition, there is a method whereby an ultrasonic probe is swept in parallel using a belt to obtain an ultrasonic image (see, for example, patent document 3 below).

A further method is one according to which a hand-held, three-dimensional ultrasonic probe is provided by rotating the electronic scanning end of an array type element (see, for example, patent document 4 below).

According to one more method, a hand-held three-dimensional ultrasonic probe for obtaining a three-dimensional, ultrasonic image is provided by mechanically oscillating a convex-shaped array type element (see, for example, patent document 5 below).

On the other hand, when an ultrasonic image for the heart, etc., is to be obtained by scanning the body surface, ultrasonic beams must be transmitted and received through a narrow area between the ribs, because of a need to avoid a lack of an ultrasonic image for the heart, which is located beneath the ribs, due to a reflection from the ribs, etc., that are located near the body surface and have a large acoustic impedance. Further, in order to acquire such a narrow ultrasonic transmission/reception area nearer the body surface, the oscillating center of an ultrasonic element must be positioned in the vicinity of the body surface, or in an area near the surface of the body.

However, according to a hand-held, mechanical scanning ultrasonic probe that performs scanning by mechanically oscillating an ultrasonic element, since it is impossible for the oscillating ultrasonic element to directly contact an organism, an acoustic coupling liquid must be sealed by a window and a probe case, and the ultrasonic element must be oscillated or rotated inside the liquid to perform scanning. For this type of ultrasonic element, the image resolution can be increased by reducing the size of an ultrasonic beam. However, the aperture for the ultrasonic element must be optimized, and based on the element size, during oscillation, adequate clearance between the element and the window must be provided. Therefore, it is difficult for an ultrasonic transmission/reception area near the surface of an organism to be reduced, or for the oscillating center of the ultrasonic element to be located either in the vicinity of the body surface or at a location near the body surface.

There is a conventional, mechanical scanning sector ultrasonic probe of this type that includes scanning means, for converting the rotation of a motor into the oscillation of a supporting member, and that for this purpose employs parallel grooves formed in the rear face of a support member pivotally attached to a shaft provided for a roller and an arm that are fixed to a rotor, and for oscillating an acoustic element, secured to the support member, by mechanically oscillating the element (see, for example, patent document 6 below).

Furthermore, there is an arrangement that employs the mechanism described in patent document 6 with an acoustic coupling liquid, in which the acoustic velocity is slower than that of the organism, so as to establish a substantially proportional relationship between the motor rotation angle and the oscillation angle of the acoustic element (see, for example, patent document 7).

There is in addition an arrangement wherein, using an arced guide rail and a belt, an ultrasonic beam is emitted between ribs, at the virtual oscillation center located in the vicinity of the body surface (see, for example, patent document 8 below).

Patent Document 1: Japanese Utility Model Application Publication After Examination No. S59-190208

Patent Document 2: Japanese Utility Model Application Publication After Examination No. S59-111110

Patent Document 3: Japanese Patent Application Publication No. S61-13942

Patent Document 4: Japanese Patent Application Publication No. H4-282136

Patent Document 5: Japanese Patent Application Publication No. H 3-184532

Patent Document 6: Japanese Utility Model Application Publication No. S59-42970

Patent Document 7: Japanese Patent Application Publication No. H7-24659

Patent Document 8: Japanese Patent Application Publication No. H6-38962

However, the apparatus described in the invention presented in patent document 1, for dedicated mammary gland diagnoses, that rotates a conventional array-type ultrasonic probe to obtain images, and is not operated while a doctor actually holds its probe like a hand-held ultrasonic probe. Furthermore, this apparatus is also not one with which a three-dimensional ultrasonic probe can be employed for diagnosing an additional area, such as the carotid artery or the thyroid.

The invention described in patent document 2, as well as the one in patent document 1, is not related to a hand-held, three-dimensional ultrasonic probe, and the equipment described is large scale and requires additional labor, such as advance preparation. Thus, diagnosis of an additional area, such as the carotid artery or the thyroid, can not be easily performed.

Further, it can be considered possible for a mechanism that uses a belt, etc., to sweep an ultrasonic element in parallel to be applied for a hand-held ultrasonic probe by employing the invention described in patent document 3. However, in a case wherein an array type element is to be swept in parallel, using, for example, a wire or a timing belt, pulleys must be arranged at either end of the element to be swept. In a case wherein structure is employed, the shape size of the organism contact portion is always larger than the mechanical sweeping range because of the width of the element and the diameters of the pulleys. Thus, this arrangement is not preferable for a hand-held three-dimensional ultrasonic probe. And especially in a case for performing a diagnosis for the carotid artery or the thyroid, a problem is that a hand-held three-dimensional ultrasonic probe can not contact a desired location for a target portion of an organism because a jaw, etc., obstructs the location.

Moreover, the invention described in patent document 4 relates to the acquisition of a three-dimensional ultrasonic image by rotation performed at the electronic scanning end of an array type element, and compared with a mechanical rotational movement near the center, rotational movement at a location separated from the rotation center is increased. Therefore, the pitch of the two-dimensional plane, which is the original data used for constructing a three-dimensional image, becomes smaller nearer the rotation center, while the pitch becomes larger as the distance from the rotation center increases. Thus, in proportion to the distance from the rotation center, the pitch of two-dimensional slices is increased, and when a three-dimensional image is formed based on image data for a position separated from the rotation center, a problem is that the resolution for the portion separated from the rotation center is lower.

Further, when rotation is performed at the electronic scanning end of an array type element, a mechanism is required for which a rotation axis is located at a position extended from the length of the array element in the electronic scanning direction. Thus, in a case wherein a diagnosis for a portion such as the carotid artery or the thyroid is to be performed, a problem is that an organism contact portion longer than the element may strike the jaw portion, making it difficult for an ultrasonic probe to contact a desired location.

Further, according to the three-dimensional ultrasonic probe presented in patent document 5 described above, since a three-dimensional image is obtained by mechanical oscillation of the convex-shaped array type element, the curvature of the organism contact portion at the tip of the probe is determined depending on the distance between the oscillation center of the element and the tip of the array type element. Therefore, when the organism contact portion is shaped so that, using mechanical scanning, the two ends there are appropriately brought into contact with a comparatively flat, superficial tissue portion of an organism, a large distance is required from the mechanical oscillation center to the tip of the array type element, and the curvature of the organism contact portion must be increased. In addition, when the distance from the mechanical oscillation center to the tip of the array type element is extended, the size of a hand-held, three-dimensional ultrasonic probe is increased, and this presents a problem in that the increase in the size and the weight of the hand-held three-dimensional ultrasonic probe make handling the probe difficult when performing a diagnosis.

Further, the invention described in patent document 6 provides a mechanism, which converts the rotational movement of the motor into the oscillation of the support member, by using parallel grooves, which are formed in the rear face of the support member, pivotally attached to the shaft provided for the roller and the arm that are secured to the rotor, and which oscillates an acoustic element secured to the support member to oscillate the element mechanically. Therefore, a problem encountered is that the oscillation angle of the element is not proportional to the rotational angle of the motor, and in a case wherein the velocity at which the motor rotates is a constant, the ultrasonic beam can not be oscillated at the same angle.

Furthermore, since sequentially the motor is rotated in one direction and the above described mechanism converts the rotational movement into oscillation, the oscillation angle of the element, i.e., the acoustic scanning angle, becomes a constant. And in a case wherein an organ, such as the heart, which provides rapid movement, is employed as an ultrasonic diagnosis object, when the motor is rotated fast, so that movement of the organ can be tracked well, for drawing an ultrasonic image, the density of acoustic scan lines may be reduced and image deterioration may occur. A period during which the organism depends on the acoustic velocity is required in order to obtain an ultrasonic echo from the organism, and oscillation at a small scanning angle is required in order to obtain an ultrasonic image of a rapidly moving organ, without deterioration of the image. However, according to the invention described in patent document 6, it is difficult for the oscillation velocity to be increased by setting an arbitrary oscillation angle. Furthermore, since an inverse proportion is established between the scanning line density and the angular oscillation velocity, a problem is that, for the above described mechanism, the angular oscillation velocity is high in the middle of the oscillation angle that is especially important, i.e., the scanning line density is lowered.

In addition, according to the invention described in patent document 6, oscillation is performed at the oscillation axis of the element that is located inside the window that contacts the organism. Because of this structure, the oscillation center of the element has to be located separate from the window that contacts the organism, i.e., separate from the organism, so that the actual acoustic scan lines are spread on the surface of the window, i.e., on the organism contact portion. Thus, a problem is that, when an organ, such as the ribs, that has a large acoustic impedance and that greatly reflects an ultrasonic beam, is present near the organism, an ultrasonic beam is interrupted by the organ, such as the ribs, and can not reach the organ present below, inside the organism.

Moreover, according to the invention described in patent document 7, the mechanism described in patent document 6 is employed with an acoustic coupling liquid, for which the acoustic velocity is slower than that for the organism; however, a complete proportional relation is not established between the motor rotational angle and the oscillation angle of the acoustic element. Furthermore, according to the invention described in patent document 7, as well as that in patent document 6, the oscillation is performed at the oscillation axis of the element that is located inside the window that contacts the organism. Because of this structure, the oscillation center of the element must be located separate from the window that contacts the organism, so that the actual acoustic scan lines are spread on the surface of the window, i.e., on the organism contact portion. Thus, there is a problem in that, when an organ, such as a rib, that has a large acoustic impedance and that greatly reflects an ultrasonic beam, is present near the organism, an ultrasonic beam will be interrupted by the organ, such as the rib, and can not reach an organ located below, inside the organism. In addition, as in patent document 6, since it is difficult to provide an improvement for time-transient tracking relative to an organ that moves rapidly, the oscillation velocity is increased by reducing the oscillation angle, and it is also difficult for the scanning line density and the oscillation velocity to be arbitrarily set in consonance with a diagnosis portion.

Moreover, according to the invention described in patent document 8, since there is a limitation on the width of the arm, which is fitted to and slides along the guide rail, and for the interference of the roller provided outside the guide rail, the roller must be arranged outside the actual element oscillation range, and the outer shape of the probe must be extended in accordance with the location of the roller. Therefore, this is a problem related to a reduction in the size and the weight of the probe. Further, when an organ, such as the heart, is to be scanned along the lower edge of the costal arch, i.e., from below the ribs, the probe must be moved from below the ribs to substantially parallel to the body surface, and the roundness of the probe due to the presence of the roller interferes with the scanning operation. In addition, since multiple parts, such as a guide rail, a plurality of rollers and a belt, are required for the mechanism, the total cost for these parts and the complicated assembly process are also problems.

DISCLOSURE OF THE INVENTION

While taking the above described points into account, one objective of the present invention is to provide a hand-held, mechanical scanning ultrasonic probe, according to which an ultrasonic element can be moved within a large curvature, wherein a scanning area having a large organism contact portion is provided, and which can be made smaller and lighter, so that it is appropriate for use for superficial tissue, such as the breast, the carotid artery and the thyroid.

Further, while taking the above described points into account, the objective of the present invention is to provide a small, light and inexpensive mechanical scanning ultrasonic probe that is appropriate for the sector scanning of an organ, such as the heart, through a narrow organism contact area, such as a gap between the ribs or the anterior fontanelle, or along the lower edge of the costal arch, i.e., from below the ribs.

Furthermore, the objective of the present invention is to provide a mechanical scanning ultrasonic probe that is appropriate for sector scanning of an organ, such as the heart, from below the ribs, and that can transmit and receive an ultrasonic beam from a narrow area of an organism in the vicinity of the body surface.

In order to achieve the objectives, an ultrasonic probe according to the present invention is characterized by comprising, in an area that is defined by a window of the ultrasonic probe and a casing thereof, and in which an acoustic coupling fluid is enclosed, a motor, secured outside the probe casing;

a first cylinder pulley, which is secured inside the probe casing, and through which a motor spindle of the motor passes;

an arm secured to the motor spindle that passes through and projects from the first cylinder pulley;

a second cylinder pulley, provided so rotatable at a pulley shaft that is secured to an end of the arm opposite a motor-spindle-secured end;

a slider bearing, secured to the second cylinder pulley;

a slider shaft, which is attached, by the slider bearing, so slidable and with which an ultrasonic element is secured, via the slider bearing, to a side opposite the motor spindle;

a guide rail in an arced shape, secured inside the probe casing, with a curvature center lying along an extension from the ultrasonic element to the motor spindle; and a roller, connected to the slider shaft to move while contacting the guide rail.

With this arrangement, the ultrasonic element inclines at the center of the curvature of the guide rail, and also starts, due to telescopic movement, the oscillation that has a large curvature at the center of the curvature of the guide rail. Thus, oscillation equivalent to that of an oscillating mechanism, which has a long arm that extends from the curvature center of the guide rail to the ultrasonic element, can be obtained, and the size of the ultrasonic probe can be reduced.

Further, the ultrasonic probe is characterized in that an elastic member is located between the slider shaft and the slider bearing, so that the roller will be pressed against a contacting face of the guide rail.

With this arrangement, while oscillating from side to side, the ultrasonic element secured to the distal end of the slider shaft performs a telescopic movement, relative to the slider bearing.

Furthermore, the ultrasonic probe is characterized in that a spring is arranged between the slider shaft and the slider bearing, so that the roller will be pressed against a slider-bearing-side face of the guide rail.

With this arrangement, while oscillating from side to side, the ultrasonic element secured to the distal end of the slider shaft performs a telescopic movement, relative to the slider bearing.

In addition, the ultrasonic probe is characterized in that a plurality of rollers are arranged in contact with the slider-bearing-side face of the guide rail and a face thereof opposite the slider-bearing-side face, respectively, so as to sandwich the guide rail.

With this arrangement, the plurality of rollers can slide along the guide rail, while sandwiching the guide rail.

Moreover, the ultrasonic probe is characterized in that the plurality of rollers arranged to sandwich the guide rail include:

a roller rotatably attached to the slider shaft; and a roller provided so that the roller and the roller attached to the slider shaft are to be drawn near each other by a spring.

With this arrangement, the plurality of rollers can slide along the guide rail, while sandwiching the guide rail.

Further, the ultrasonic probe is characterized in that:

the guide rail is prepared at a plurality of locations, so that the roller is sandwiched between the guide rails.

With this arrangement, the rollers can slide along the guide rails, while sandwiched between the guide rails.

Also, the ultrasonic probe is characterized in that a plurality of the rollers are mounted and sandwiched between the guide rails, so that the rollers, impelled by springs, repel each other.

With this arrangement, since the rollers, impelled by springs, repel each other, wobbling of the guide rails, relative to the groove, can be eliminated.

Further, the ultrasonic probe is characterized in that:

a ratio of one to two is employed as a ratio of a diameter of the first cylinder pulley to a diameter of the second cylinder pulley; and a length of the guide rail from the center of the curvature to the motor spindle is set equal to a length of the arm extended from the motor spindle to the second cylinder pulley.

With this arrangement, because of the inclination of the arm, the second cylinder pulley is rotated ½ way around the second cylinder pulley, in a direction opposite the rotational direction of the motor spindle, and when the motor spindle is rotated, the slider shaft, to which the ultrasonic element is secured, oscillates at the curvature center of the guide rail, while constantly maintaining the rotational angle of ½ for the motor spindle.

Furthermore, the ultrasonic probe is characterized in that a length of the arm extending from the motor-spindle-secured end to the other end, where the pulley shaft is secured, is set equal to or greater than a length extending from the pulley shaft to the roller shaft.

With this arrangement, since the center of the curvature of the guide rail is located farther from the motor spindle, a mechanism for oscillating the ultrasonic element, along a trajectory having a large curvature radius, can be made more compactly.

In addition, the ultrasonic probe is characterized in that:

the ultrasonic element that is secured to the slider shaft is an electronic-scanning, array-type ultrasonic element; and when mechanical scanning is performed in a direction perpendicular to an electronic scanning direction of the array-type ultrasonic element, scanning of two cross sections perpendicular to each other is enabled by using both the electronic scanning and the mechanical scanning.

With this arrangement, a three-dimensional ultrasonic probe that performs mechanical scanning using a large curvature, which makes it easy for the probe to closely contact the superficial tissue, can be obtained.

In order to achieve the above objectives, an ultrasonic probe according to the present invention is characterized by comprising, in an area which is defined by a window of the ultrasonic probe and an outer case thereof, and wherein an acoustic coupling fluid is enclosed, a first pulley, which is secured inside a probe casing, outside of which a motor is secured and through which a motor spindle of the motor is passed;

an arm, secured to the motor spindle that is passed through and projected from the first pulley;

a second pulley, provided so rotatable at a pulley shaft that is secured to an end of the arm opposite a motor-spindle secured end;

a connecting member, for connecting the first pulley to the second pulley;

a slider bearing, secured to the second pulley;

a slider shaft, which is mounted, by the slider bearing, so slidable, and to one end of which an ultrasonic element is secured;

a roller shaft, provided for the other end of the slider shaft;

a guide rail in an arced shape, which is secured inside the probe casing, and for which a curvature center is present on a line extended from a roller-shaft-secured end of the slider shaft in a direction toward the ultrasonic element; and a roller moving, via the roller shaft connected to the slider shaft, while contacting the guide rail.

With this arrangement, when the motor spindle begins to rotate or oscillate, the ultrasonic element moves along an oscillation trajectory by employing, as the center of oscillation, the curvature center of the guide rail. Further, a mechanism can be obtained for which the center, for sector acoustic scanning, is located on the obverse surface of the window where the acoustic coupling liquid is enclosed, or around the surface. Also, an ultrasonic probe can be provided whereby a constant proportional relationship, between the rotational angle of the motor and the oscillation angle of the acoustic element, and a constant distance, between the acoustic element and the window, can be maintained, and whereby the ultrasonic beam can be transmitted or received through a narrow area near the body surface of the organism.

Further, the ultrasonic probe is characterized in that an elastic member is located between the slider shaft and the slider bearing, so that the roller will be pressed against a contacting face of the guide rail.

With this arrangement, while oscillating from side to side, the ultrasonic element secured to the distal end of the slider shaft performs a telescopic movement, relative to the slider bearing.

Furthermore, the ultrasonic probe is characterized in that a spring that is the elastic member is arranged between the slider shaft and the slider bearing, so that the roller will contact a slider-bearing-side face of the guide rail.

With this arrangement, while oscillating from side to side, the ultrasonic element secured to the distal end of the slider shaft performs a telescopic movement, relative to the slider bearing.

Further, the ultrasonic probe is characterized in that the spring, which is the elastic member, is located between the slider shaft and the slider bearing, so that the spring brings the roller into contact the guide rail on a side opposite the slider bearing.

With this arrangement, while oscillating from side to side, the ultrasonic element secured to the distal end of the slider shaft performs a telescopic movement, relative to the slider bearing.

In addition, the ultrasonic probe is characterized in that a plurality of rollers are arranged in contact with the slider-bearing-side face of the guide rail and a face thereof opposite the slider-bearing-side face, respectively, so as to sandwich the guide rail.

With this arrangement, the plurality of rollers can slide along the guide rail, while sandwiching the guide rail.

Moreover, the ultrasonic probe is characterized in that the plurality of rollers arranged to sandwich the guide rail include:

a roller rotatably attached to the slider shaft; and a roller provided so that the roller and the roller attached to the slider shaft are to be drawn near each other by a spring.

With this arrangement, the plurality of rollers can slide along the guide rail, while sandwiching the guide rail.

Further, the ultrasonic probe is characterized in that:

the guide rail is prepared at a plurality of locations, so that the roller is sandwiched between the guide rails.

With this arrangement, the rollers can slide along the guide rails, while sandwiched between the guide rails.

Also, the ultrasonic probe is characterized in that a plurality of the rollers are mounted and sandwiched between the guide rails, so that the rollers, impelled by springs, repel each other.

With this arrangement, since the rollers, impelled by springs, repel each other, wobbling of the guide rails, relative to the groove, can be eliminated.

Further, the ultrasonic probe is characterized in that:

a ratio of one to two is employed as a ratio of a diameter of the first pulley to a diameter of the second pulley; and a length of the guide rail from the center of the curvature to the motor spindle is set equal to a length of the arm extended from the motor spindle to the second pulley.

With this arrangement, because of the inclination of the arm, the second pulley is rotated ½ way around the second pulley, in a direction opposite the rotational direction of the motor spindle, and when the motor spindle is rotated, the slider shaft, to which the ultrasonic element is secured, oscillates at the curvature center of the guide rail, while constantly maintaining the rotational angle of ½ for the motor spindle.

Furthermore, the ultrasonic probe is characterized in that a length of the arm extending from the motor-spindle-secured end to the end, where the pulley shaft is secured, is set equal to or greater than a length extending from the pulley shaft to the roller shaft.

With this arrangement, since the center of the curvature of the guide rail is located farther from the motor spindle, a mechanism for oscillating the ultrasonic element, along a trajectory having a large curvature radius, can be made more compactly.

In addition, the ultrasonic probe is characterized in that:

the ultrasonic element that is secured to the slider shaft is an electronic-scanning, array-type ultrasonic element; and when mechanical scanning is performed in a direction perpendicular to an electronic scanning direction of the array-type ultrasonic element, scanning of two cross sections perpendicular to each other is enabled by using both the electronic scanning and the mechanical scanning.

With this arrangement, a three-dimensional ultrasonic probe that performs mechanical scanning using a large curvature, which makes it easy for the probe to closely contact the superficial tissue, can be obtained.

To achieve the above objectives, an ultrasonic probe according to the present invention comprises:

a motor;

a first arm, fitted to a rotary shaft of the motor so rotatable in accordance with a rotation of the rotary shaft;

a second arm, to the distal end of which an ultrasonic element is attached;

a grooved portion formed in the second arm, for storing a distal end of the first arm, so that the distal end of the first arm is shifted parallel to the second arm;

a third arm, constituting a linking mechanism having two rotatable ends, one end of which is rotatably attached to the second arm by a first shaft that is mounted on an end of the second arm, opposite the end to which the ultrasonic element is secured, and the other end of which is rotatably attached to the first arm by a second shaft, located at an arbitrary position between a rotational center of the first arm and the grooved portion of the second arm; and a spring, for drawing an end portion, where the second arm and the third arm are connected, along a motor-spindle, perpendicular line, toward a side opposite the end of the second arm where the ultrasonic element is secured, wherein the second arm, to which the ultrasonic element is attached, is oscillated in accordance with the rotation of the rotary shaft of the motor.

With this arrangement, since the first arm secured to the motor spindle is rotated at the motor spindle, the distal end of the first arm oscillates the second arm, while being shifted parallel along the grooved portion that is formed in the second arm. The first shaft secured end of the third arm is rotatably attached to the first shaft secured end of the second arm, and the second shaft secured end of the third arm is rotatably attached in the middle of the first arm. Thus, the distal end of the first arm, the second shaft secured end of the third arm and the first shaft secured end of the third arm form a triangle. When the first arm is rotated in this arrangement, the distal end of the second arm can be oscillated along a trajectory that has a larger curvature than when it is oscillated at the motor spindle.

Moreover, the ultrasonic probe is characterized in that:

a length from a coupling point of the third arm that joins the first arm to a coupling point that joins the second arm is set equal to a length from a coupling point of the first arm that joins the third arm to a coupling point that joins the second arm;

the spring is arranged between an intersection point of the motor-spindle, perpendicular line with a trajectory of the distal end of the first arm, on a side opposite the end where the ultrasonic element is secured, and an end portion at which the second arm and the third arm are connected using the first shaft; and the triangle formed using the individual coupling points is an isosceles triangle.

With this arrangement, when the first arm is pivoted at a predetermined angle, the distal end of the second arm is rotated ½ of the predetermined angle by employing, as a virtual center point, the center point of a circular arc trajectory drawn by the third arm and the second arm during oscillation. Thus, the oscillation trajectory that is obtained using a long arm that oscillates at the virtual center point can be provided using a short arm.

Also, the ultrasonic probe is characterized in that the second shaft, which connects the first arm to the third arm, is located near the distal end side of the first arm from an intermediate point at a distance from the rotational center of the first arm to the distal end thereof.

With this arrangement, when the first arm is oscillated, the distance at which the coupling point of the third arm and the second arm is projected, from outside the motor spindle, can be shortened, and the scanning mechanism for oscillating the ultrasonic element can be further downsized.

Further, the ultrasonic probe is characterized in that:

a speed reduction mechanism is provided for the rotary shaft of the motor; and the first arm is oscillated while the rotational center of the first arm is secured to the rotary shaft, the speed of which is reduced by the speed reduction mechanism.

With this arrangement, since the rotation of the motor is controlled based on a rotation angle that is much larger than the oscillation angle of the ultrasonic element, the position of the element portion can be controlled more precisely, even using a pulse motor having a large pitch or an encoder having a large pitch.

Furthermore, the ultrasonic probe is characterized in that the ultrasonic element is an electronic scanning type element, and is to be mechanically oscillated in an electronic scanning direction and in a direction perpendicular to the electronic scanning direction.

With this arrangement, the ultrasonic probe that enables three-dimensional scanning by performing electronic scanning and mechanical scanning can be provided.

To achieve the above objectives, an ultrasonic probe according to the present invention comprises:

a motor;

a first arm, fitted to a rotary shaft of the motor so rotatable in accordance with a rotation of the rotary shaft;

a second arm, to the window side distal end of which an ultrasonic element is attached;

a grooved portion formed in the second arm, for storing a distal end of the first arm, so that the distal end of the first arm is shifted parallel to the second arm;

a third arm, constituting a linking mechanism having two rotatable ends, one end of which is rotatably attached to the second arm by a first shaft that is provided between a secured end, of the ultrasonic element that is mounted on the second arm, and the grooved portion, and the other end of which is rotatably attached to the first arm by a second shaft that is located at an arbitrary position between a rotational center of the first arm and the grooved portion of the second arm; and a spring, for drawing an end portion, where the second arm and the third arm are connected, along a motor-spindle, perpendicular line, toward the end of the second arm where the ultrasonic element is secured, wherein the second arm, to which the ultrasonic element is attached, is oscillated in accordance with the rotation of the rotary shaft of the motor.

With this arrangement, since the first arm secured to the motor spindle is rotated at the motor spindle, the distal end of the first arm oscillates the second arm, while being shifted parallel along the grooved portion that is formed in the second arm. The first-shaft secured end of the third arm is rotatably attached to the first shaft, which is provided between the end of the second arm, to which the ultrasonic element is secured, and the grooved portion, while the second-shaft secured end of the third arm is rotatably attached to the second shaft, which is provided between the distal end of the first arm and the rotational center. Thus, the distal end of the first arm, the second-shaft secured end of the third arm and the first-shaft secured end of the third arm form a triangle, and the portion where the second arm and the third arm are rotatably connected by the first shaft is drawn, by the spring, toward the end of the second arm where the ultrasonic element is secured. With this arrangement, when the first arm is rotated, the ultrasonic element secured to the window side of the second arm can oscillate by employing the vicinity of the window as the virtual oscillation center.

Moreover, the ultrasonic probe is characterized in that:

a length from a coupling point of the third arm that joins the first arm to a coupling point that joins the second arm is set equal to a length from a coupling point of the first arm that joins the third arm to a coupling point that joins the second arm;

the spring is arranged between an intersection point of the motor-spindle, perpendicular line with a trajectory of the distal end of the first arm, on the side of the end where the ultrasonic element is secured, and an end portion at which the second arm and the third arm are connected using the first shaft; and the triangle formed using the individual coupling points is an isosceles triangle.

With this arrangement, when the first arm is pivoted at a predetermined angle, the distal end of the second arm is turned ½ of the predetermined angle by employing, as a virtual center point, an intersection point of the circular arc trajectory, drawn by the distal end of the first arm, with the perpendicular line, drawn downward from the motor spindle in a drawing. Therefore, oscillation can be performed using the virtual oscillation center.

Also, the ultrasonic probe is characterized in that the second shaft, which connects the first arm to the third arm, is located near the distal end side of the first arm from an intermediate point at a distance from the rotational center of the first arm to the distal end thereof.

With this arrangement, when the first arm is oscillated, the distance at which the coupling point of the third arm and the second arm is projected, from outside the motor spindle, can be shortened, and the ultrasonic element and the mechanism can be arranged inside the oscillation center point of the ultrasonic element, i.e., inside the vicinity of the window. Thus, the arrangement wherein the ultrasonic element does not collide with the window during oscillation can be provided.

Further, the ultrasonic probe is characterized in that:

a speed reduction mechanism is provided for the rotary shaft of the motor; and the rotational center of the first arm is secured to the rotary shaft, the speed of which is reduced by the speed reduction mechanism, and the motor is arranged separate from the window of the ultrasonic probe to perform oscillation.

With this arrangement, since the rotation of the motor is controlled based on a rotation angle that is much larger than the oscillation angle of the ultrasonic element, the position of the element portion can be controlled more precisely, even using a pulse motor having a large pitch or an encoder having a large pitch. In addition, since the speed reduction mechanism is interposed between the motor spindle and the first arm, instead of the motor spindle being directly secured to the first arm, the motor can be arranged separate from and above the window of the ultrasonic probe, without being projected from the window that is a body surface contact portion.

Furthermore, the ultrasonic probe is characterized in that:

the ultrasonic element is an electronic scanning type element, and is to be mechanically oscillated in an electronic scanning direction and in a direction perpendicular to the electronic scanning direction, or is characterized in that:

the ultrasonic element is a single element, which is to be independently rotated or oscillated to perform mechanical scanning, and is to be mechanically oscillated in a direction perpendicular to a direction for the mechanical scanning.

With this arrangement, the ultrasonic probe that enables three-dimensional scanning can be provided.

According to the present invention, since a short arm, i.e., a small oscillating mechanism, can be employed as a mechanism for mechanically oscillating an ultrasonic element along a large oscillating curvature, the size and the weight of the hand-held ultrasonic probe can be reduced, thereby providing an ultrasonic probe for which diagnosis operability is improved. Specifically, such a hand-held mechanical scanning ultrasonic probe can be provided that satisfies conflicting requests for an ultrasonic probe used for a diagnosis performed for superficial tissue, i.e., requests for the provision of a large visual field in the vicinity of a large body surface and for a reduction in the size and the weight, and that is appropriate for use for superficial tissue, such as the breast, the carotid artery or the thyroid.

Further, according to the present invention, the above described arrangement can provide effects such that ultrasonic scanning can be performed via a narrow area on the body contact face, a constant relationship can be maintained between the rotational angle of a drive source, such as a motor, and the rotational angle of the ultrasonic element, and when the rotational angle of a drive source, such as the motor, is maintained, acoustic scan lines can be kept at a constant density. In addition, since a constant relationship is always maintained between the rotational angle of the motor spindle and the oscillating angle of the ultrasonic element, the motor spindle need only be rotated at a steady velocity, so that the oscillating velocity of the ultrasonic element can be constant, and the density of the scanning lines for forming an ultrasonic image can be maintained. Further, when the forward and reverse rotation of the motor spindle is performed at a small angle, the acoustic scan line density can be uniformly increased to extract a specific portion of an organ that rapidly moves. Based on the above described effects, a mechanical scanning ultrasonic probe can be obtained that is appropriate for use when the ultrasonic image of the heart is to be obtained through the ribs, or when the ultrasonic diagnostic image of the brain is to be obtained via the anterior fontanelle of a newborn baby.

According to the present invention, since a short arm, i.e., a small oscillating mechanism, can be employed as a mechanism for mechanically oscillating an ultrasonic element along a large oscillating curvature, the size and the weight of the hand-held ultrasonic probe can be reduced, thereby providing an ultrasonic probe for which diagnosis operability is improved. Specifically, such a hand-held mechanical scanning ultrasonic probe can be provided that satisfies conflicting requests for an ultrasonic probe used for a diagnosis performed for superficial tissue, i.e., requests for the provision of a large visual field in the vicinity of a large body surface and for a reduction in the size and the weight, and that is appropriate for use for superficial tissue, such as the breast, the carotid artery or the thyroid.

Moreover, according to the present invention, when scanning is performed by mechanically oscillating the ultrasonic element in accordance with the rotation of the motor, the trajectory of the oscillation of the ultrasonic element can be drawn by employing, as the center, the vicinity of the window that contacts the organism. Further, when the center point in the sector radiation of the ultrasonic element is set in the vicinity of the window, obstacles along the ultrasonic transmission/reception path can be avoided to perform scanning.

BEST MODE FOR CARRYING OUT THE INVENTION

<First Mode>

Figure 1:
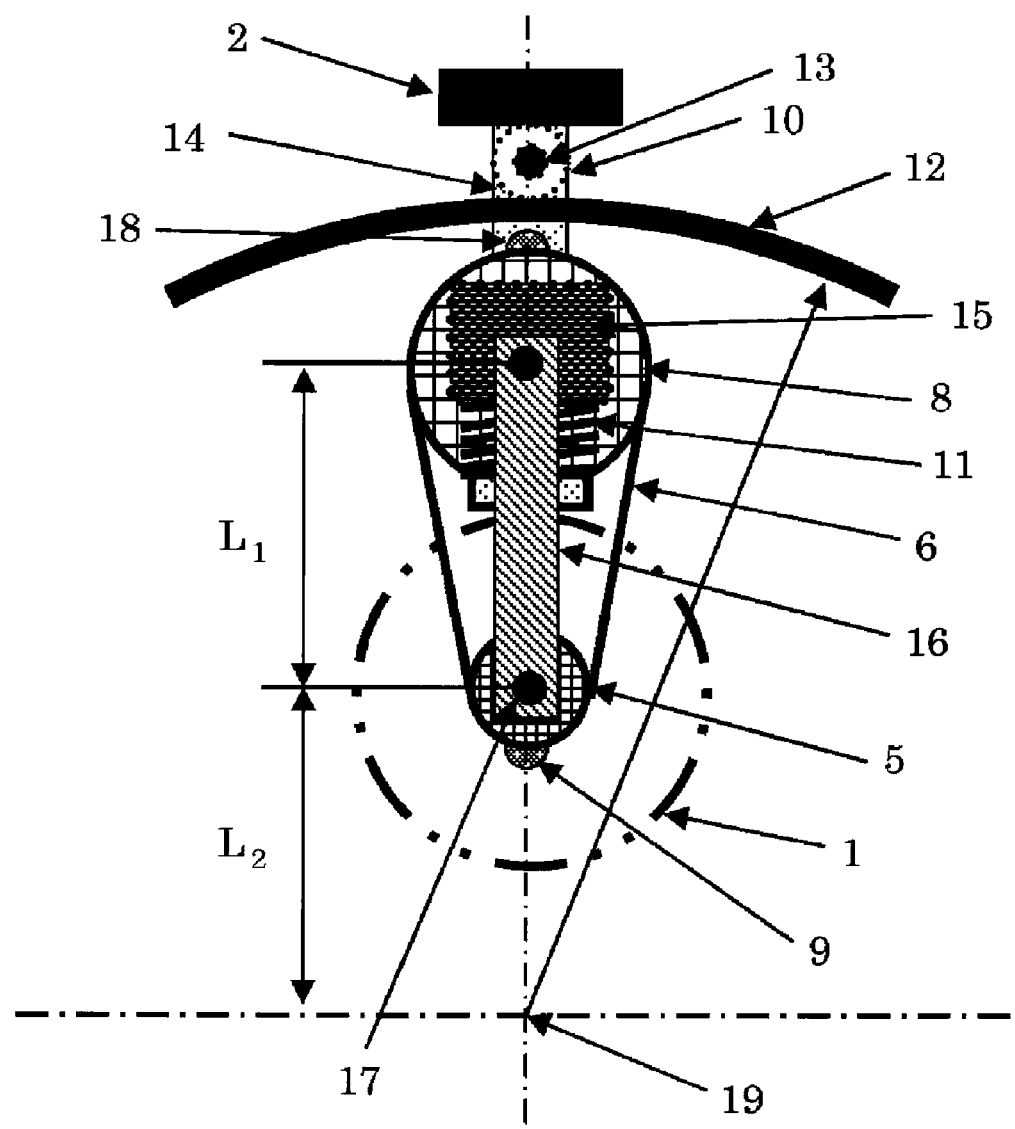
FIG. 1 is a front view of an ultrasonic probe according to a first mode of the present invention.
Figure 2:
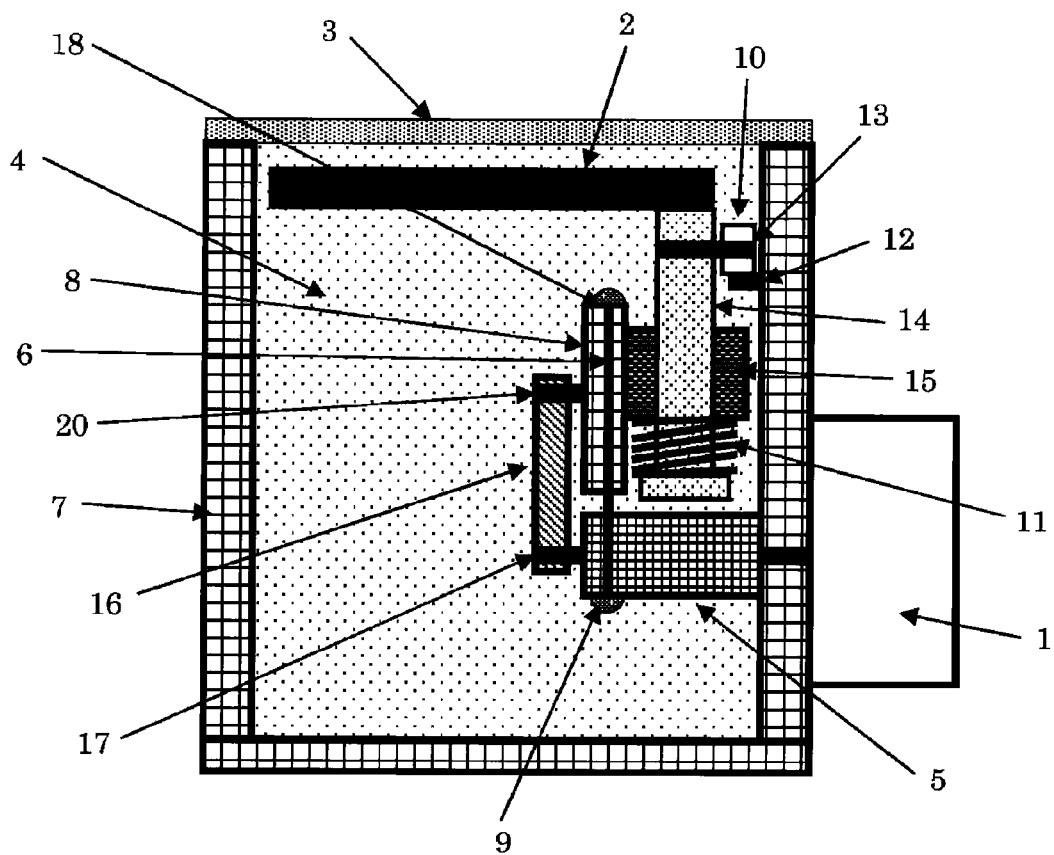
FIG. 2 is a side view of the ultrasonic probe according to the first mode of the present invention.

Ultrasonic probes according to the modes of the present invention will now be described while referring to drawings. FIGS. 1 and 2 are a front view and a side view of an ultrasonic probe according to a first mode of the present invention. In FIG. 2, a motor spindle 17 of a motor 1 is to be rotated or oscillated upon externally receiving an electric drive signal from ultrasonic diagnostic equipment (not shown). An ultrasonic element 2 is stored in an area that is enclosed by a window 3 and a probe casing 7, and this area is filled with an acoustic coupling liquid 4 for transferring an ultrasonic signal that is transmitted or received by the ultrasonic element 2.

The motor spindle 17 of the motor 1, which is secured to the outside of the probe casing 7, passes via a sealant, such as material used as an oil seal (not shown), through the probe casing 7 and a first cylinder pulley 5 that is secured to the probe casing 7 and to an arm 16 arranged within the probe casing 7. A pulley shaft 20 is secured to the other end of the arm 16, and a second cylinder pulley 8 is mounted so rotatable around the pulley shaft 20. The first cylinder pulley 5 and the second cylinder pulley 8 are secured using a wire 6 and, respectively, a first wire fastening device 9 and a second wire fastening device 18.

A slider bearing 15 is secured to the second cylinder pulley 8, and a slider shaft 14 is fitted, so slidable, on the slider bearing 15. A roller shaft 13 is secured to the slider shaft 14, and a roller 10 is mounted so rotatable around the roller shaft 13. In this arrangement, a spring 11, which is arranged between a part of the slider shaft 14 and a part of the slider bearing 15, exerts a constant force to draw the roller 10 down to contact a guide rail 12 located inside the probe casing 7.

With such an arrangement, wherein the first cylinder pulley 5 and the second cylinder pulley 8 are held by the wire 6, and wherein the first cylinder pulley 5 is secured to the probe casing 7, when the motor spindle 17 rotates and inclines the arm 16, at the same time, the second cylinder pulley 8 begins to be rotated around the pulley shaft 20. Since the slider bearing 15 is secured to the second cylinder pulley 8, the slider bearing 15, as well as the second cylinder pulley 8, is inclined and rotated at the same time as the motor spindle 17 is rotated. The slider shaft 14, slidably attached to the slider bearing 15, also performs the same movements. Further, since the roller 10 that is rotatably attached to the roller shaft 13, which is fixed to the slider shaft 14, is constantly drawn down by the spring 11 to make contact with the guide rail 12, located inside the probe outer case 7, the slider 14, in addition to inclination and rotation, performs a telescopic movement along the shape of the guide rail 12 as the motor spindle 17 is rotated.

At this time, when, as illustrated in FIG. 1, 19 denotes a guide rail curvature center for the guide rail 12, assume that a distance $L_2$ from the guide rail curvature center 19 to the center of the first cylinder pulley 5, i.e., a distance to the center of the motor spindle 17, is set equal to a distance $L_1$ from the center of the first cylinder pulley 5 to the center of the second cylinder pulley 8, and that a ratio of the diameter of the first cylinder pulley 5 to the diameter of the second cylinder pulley 8 is defined as a ratio of one to two.

Figure 3:
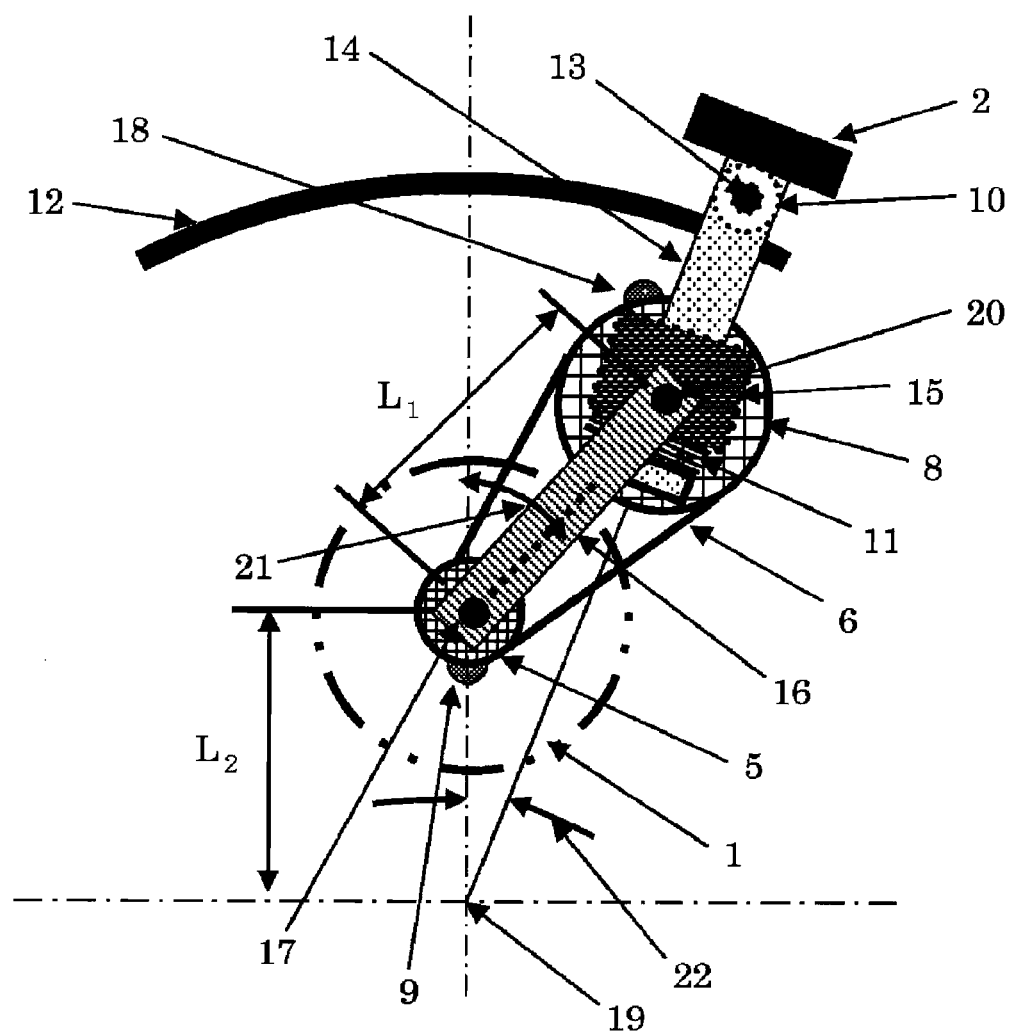
FIG. 3 is a front view for explaining the oscillation state of the ultrasonic probe according to the first mode of the present invention.

The state wherein the ultrasonic element 2 is oscillated will now be described in detail while referring to FIG. 3. According to the arrangement of this invention, since the length $L_2$, from the guide rail curvature center 19 to the center of the motor spindle 17, is set equal to the length $L_1$, from the center of the point of the arm 16 secured to the motor spindle 17 to the center of the second cylinder pulley 8, an isosceles triangle is formed by the center of the second cylinder pulley 8, the center of the motor spindle 17 and the guide rail curvature center 19, so that a relationship of two to one is constantly established between a motor spindle rotational angle 21 and an element oscillating angle 22 in FIG. 3. Furthermore, since a ratio of one to two is employed for the diameter of the first cylinder pulley 5 and the diameter of the second cylinder pulley 8, and the first cylinder pulley 5 and the second cylinder pulley 8 are held by a wire or a steel band belt, the second cylinder pulley 8 is rotated, due to the inclination of the arm 16, by ½ a rotation at the second cylinder pulley 8 in a direction opposite the rotation direction for the motor spindle 17.

Therefore, when the motor spindle 17 is rotated, the slider shaft 14 to which the ultrasonic element 2 is fitted initiates oscillation by employing the guide rail curvature center 19 as the oscillation center, while maintaining a displacement that is ½ the motor spindle rotation angle 21.

Furthermore, the roller 10 is provided for the slider shaft 14 to which the ultrasonic element 2 is secured, so that by means of the spring 11, the roller 10 is constantly held against or brought into contact with the guide rail 12. Thus, while being oscillated from side to side, the ultrasonic element 2 slides relative to the slider bearing 15, and performs a telescopic movement, i.e., the distance from the ultrasonic element 2 to the pulley shaft 20 of the second cylinder pulley 8, to which the slider bearing 15 is fixed, is increased or reduced.

As described above, the ultrasonic element 2 inclines at the guide rail curvature center 19, and also oscillates, due to a telescopic movement, with a large curvature at the guide rail curvature center 19. Therefore, it is possible to obtain the same oscillation as provided by an oscillation mechanism that has a long arm extended from the guide rail curvature center 19 to the ultrasonic element 2, and the size of the ultrasonic probe can be reduced.

For this mode, an arrangement has been employed wherein the roller 10 is drawn toward the guide rail 12 by the spring 11 provided on the side opposite the slider bearing 15, i.e., wherein the spring 11 is employed to hold the roller 10 against the face of the guide rail 12 opposite the slider bearing side. However, the arrangement wherein the roller 10 is arranged inside the guide rail 12 (on the slider bearing side) and is drawn down by the spring 11, i.e., the arrangement wherein the spring 11 is employed to hold the roller 10 against the slider bearing side face of the guide rail 12, may be employed. Further, the roller 10 has been made rotatable at the roller shaft 13 in order to reduce sliding resistance. However, a Teflon (registered trademark) resin that has a low sliding resistance may be employed as the material for the guide rail 12 and the roller 10, and the roller 10 need not always be rotatable at the roller shaft 13.

Moreover, as a method for maintaining the roller 10 contact with the guide rail 12, the guide rail may be sandwiched by two or more rollers. As another arrangement, two guide rails 12 may be provided to sandwich the roller in between. In this case, two or more rollers, impelled by springs, may be attached so they repel each other, in order to remove the unsteadiness of the rollers in the grooves of the guide rails.

Further, according to the arrangement described for this mode, the ultrasonic element 2 is oscillated constantly at one point at the center of the inclination angle of the ultrasonic element 2, and the same center position has been employed to draw the trajectory for oscillation of the ultrasonic element 2. However, in a case wherein the center of the oscillation angle need not be the same as the center of the oscillation trajectory, it is not always a requirement that the length from the guide rail curvature center 19 to the center of the motor spindle 17 be equal to the length from the center of the motor spindle 17 to the center of the second cylinder pulley 8, and that a ratio for the diameter of the first cylinder pulley 5 to the diameter of the second cylinder pulley 8 be a ratio of one to two.

In addition, the ultrasonic element 2 may be a single element, and the ultrasonic probe may be a mechanical type that employs the above oscillating mechanism to perform mechanical scanning. However, when the ultrasonic element 2 of an electronic scanning type is arranged to perform electronic scanning in a direction perpendicular to the mechanical oscillation direction, an ultrasonic probe that performs electronic scanning and mechanical scanning and obtains a three-dimensional ultrasonic image can be provided.

Also, when the length of the arm 16 from the end where the motor spindle 17 is secured to the end where the pulley shaft 20 is secured is equal to or greater than the length of the pulley shaft 20 to the center of the roller 10, the guide rail curvature center 19 is located more farther from the motor spindle 17. Thus, the mechanism that oscillates the ultrasonic element 2 along a trajectory having a large curvature radius can be further downsized.

Moreover, when an electronic scanning array element is employed as the ultrasonic element 2, and the above described mechanism is employed to perform mechanical scanning in a direction perpendicular to the electronic scanning direction of the array element, a three-dimensional ultrasonic probe can be obtained that performs mechanical scanning with a large curvature, with which it is easy for the probe to closely contact superficial tissue.

<Second Mode>

Figure 4:
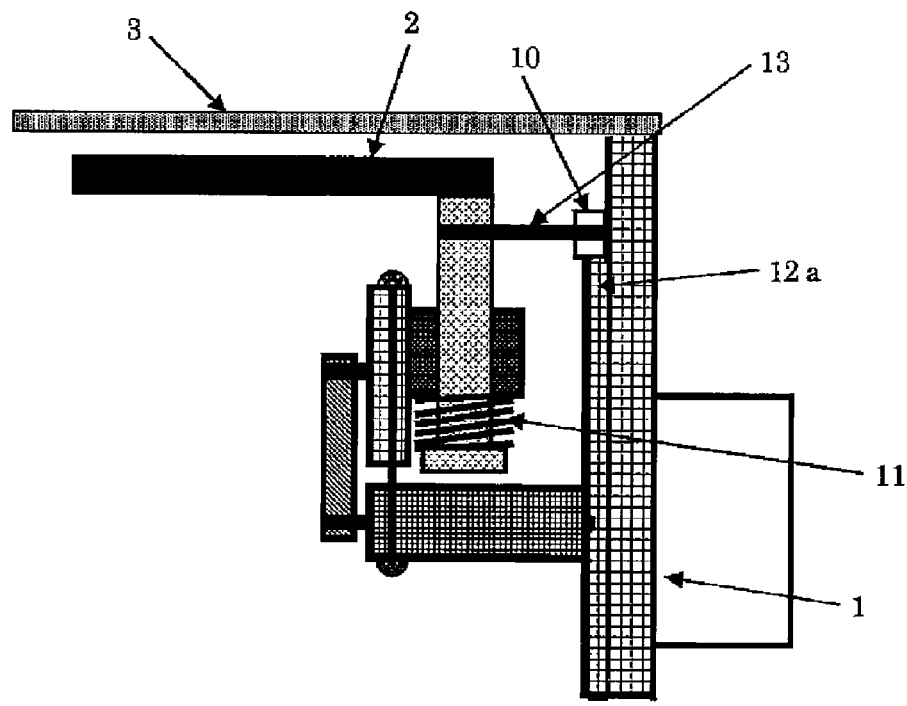
FIG. 4 is a side view of an ultrasonic probe according to a second mode of the present invention.

An ultrasonic probe according to a second mode of the present invention is illustrated in FIG. 4. The same reference numerals as used in the first mode are also employed to describe the corresponding arrangement. In the second mode, a point greatly different from the first mode is that a guide rail 12a is integrally formed with a probe casing 7. According to this arrangement, since there is no undercut portion, in a case wherein the probe casing 7 is to be formed using a mold, the mold for the probe casing 7 can be raised toward the window 3 after the probe casing 7 has been formed. Therefore, the use of a slider mold is not required, the expenditure for a mold is reduced, and the probe can be manufactured at a low cost. In addition, since a roller 10 is constantly pressed toward the guide rail 12*a* by a spring 1, a constant distance between an ultrasonic element 2 and the window 3 can be maintained.

<Third Mode>

Figure 5:
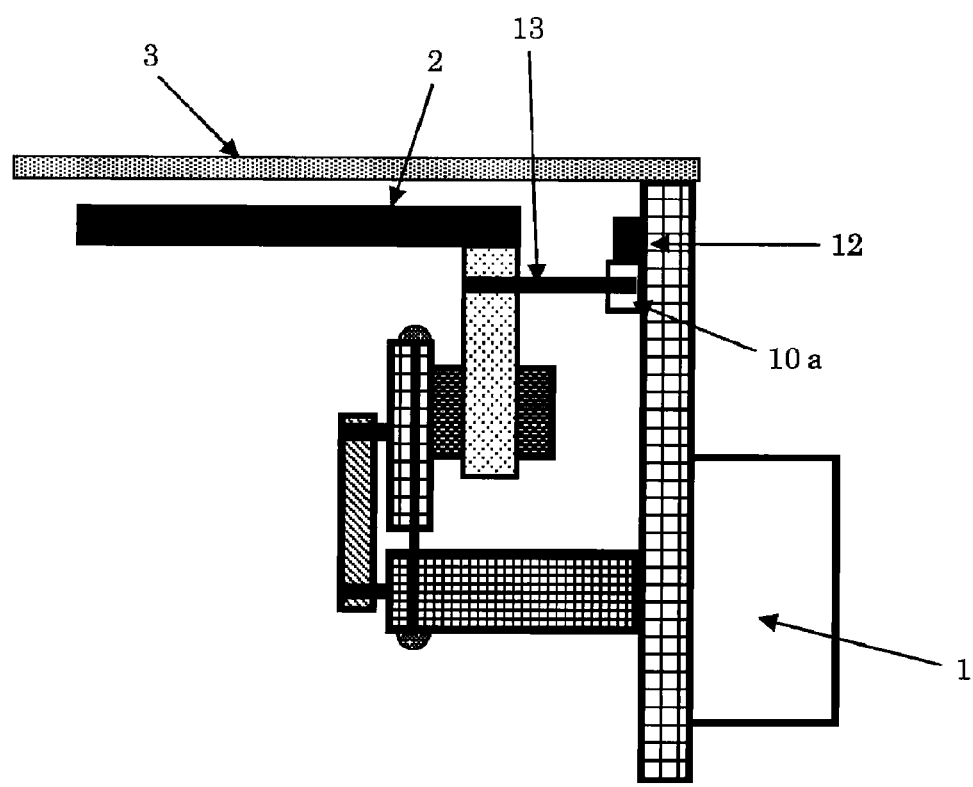
FIG. 5 is a side view of an ultrasonic probe according to a third mode of the present invention.

An ultrasonic probe according to a third mode of the present invention is illustrated in FIG. 5. The same reference numerals as used in the above described modes are employed to describe the corresponding arrangement. The ultrasonic probe of this mode is effective for a case wherein for use a window side is directed downward. An ultrasonic element 2 can perform oscillation while, impelled by its own weight, a roller 10*a* contacts a guide rail 12 on the window 3 side. Thus, without a spring 11 being required, a constant distance can be maintained between the ultrasonic element 2 and the window 3, and oscillation of the ultrasonic element 2 is enabled. Further, according to the structure of this mode, the distance between the ultrasonic element 2 and the window 3 is always maintained, even in a case wherein the probe is dropped, and it is thus possible that, should the probe be dropped, the ultrasonic element 2 will avoid colliding with the window 3 and being damaged.

<Fourth Mode>

Figure 6:
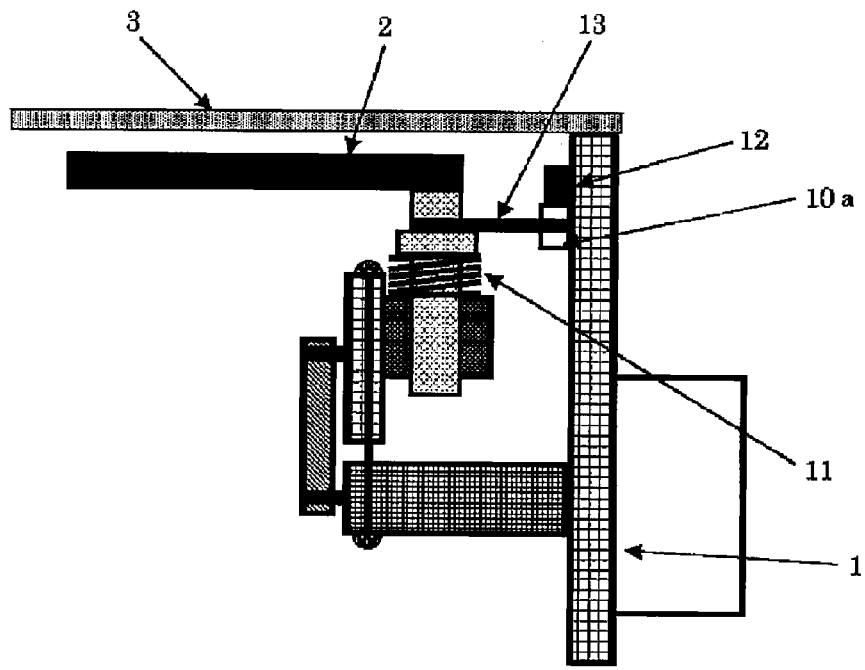
FIG. 6 is a side view of an ultrasonic probe according to a fourth mode of the present invention.

An ultrasonic probe according to a fourth mode of the preset invention is illustrated in FIG. 6. The same reference numerals as used in the above modes are employed to describe the corresponding arrangement. In the ultrasonic probe of this mode, in addition to the third mode, a constant distance between an ultrasonic element 2 and a window 3 can be maintained by the force exerted by a spring 11. Thus, in a case wherein the probe is to be moved while upside down and in contact with an organism, the same distance between the ultrasonic element 2 and the window 3 can be maintained for all the postures of the probe.

<Fifth Mode>

Figure 7:
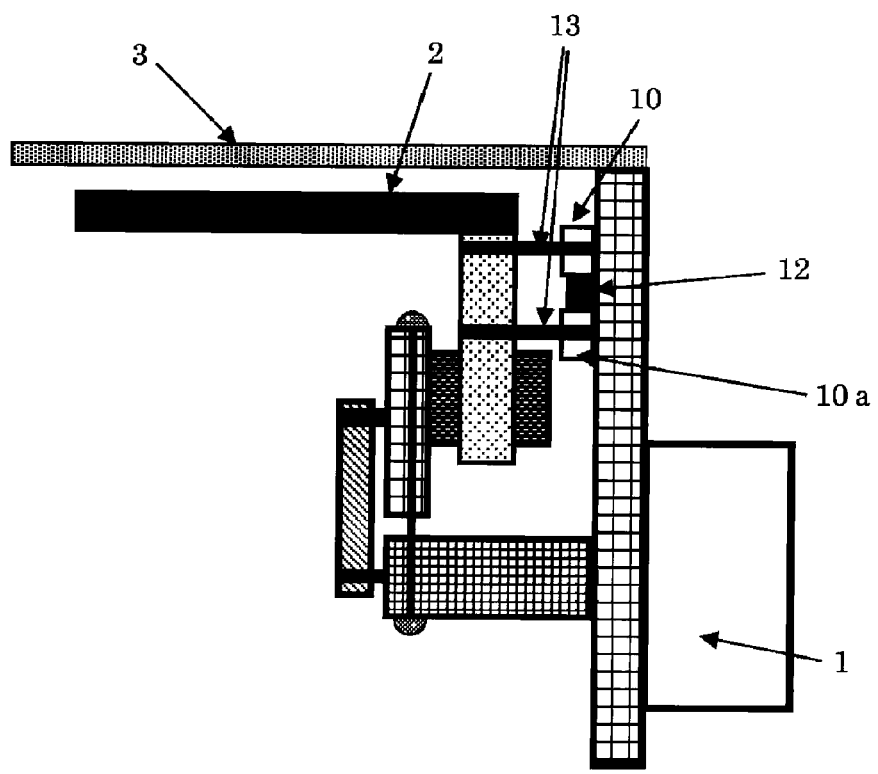
FIG. 7 is a side view of an ultrasonic probe according to a fifth mode of the present invention.

An ultrasonic probe according to a fifth mode of the present invention is illustrated in FIG. 7. The same reference numerals as used in the above modes are employed to describe the corresponding arrangement. According to the arrangement of the ultrasonic probe of this mode, a guide rail 12 is arranged so sandwiched between two rollers 10, 10*a*, and using these two rollers, the distance between an ultrasonic element 2 and a window 3 is maintained along the guide rail 12. Therefore, it is possible to avoid a phenomenon such that, when the slider shaft, i.e., the ultrasonic element 2, is extended or retracted by the urging force of the spring 11, the force exerted to press the roller 10 against the guide rail 12 will vary, depending on the oscillation position. Thus, it is also possible to avoid a phenomenon wherein the mechanical load imposed on the motor 1 for oscillation is changed, depending on the oscillation angle, and accordingly, load change need not be considered when the motor 1 for oscillating the ultrasonic element 2 is controlled.

<Sixth Mode>

Figure 8:
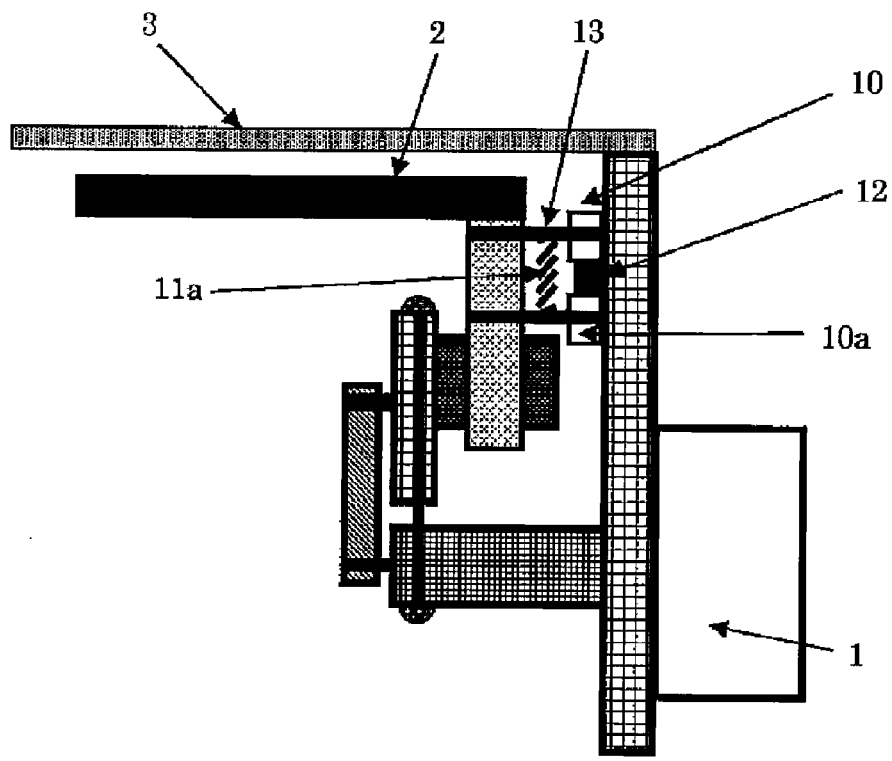
FIG. 8 is a side view of an ultrasonic probe according to a sixth mode of the present invention.

An ultrasonic probe according to a sixth mode of the present invention is illustrated in FIG. 8. The same reference numerals as used in the above modes are employed to describe the corresponding arrangement. According to the arrangement of the ultrasonic probe of this mode, a guide rail 12 is sandwiched between two rollers 10, 10*a*, and these two rollers 10, 10*a* are drawn by a spring 11*a*. Therefore, since the rollers 10, 10*a* are drawn in toward each other by the force exerted by the spring 11*a*, even when the width of the guide rail 12 sandwiched between the two rollers 10, 10*a* is slightly un-uniform, a load that will be increased in a case where there is a wide guide rail can be reduced, and also, the wobbling that will occur in a case where there is a narrow guide rail can be reduced.

<Seventh Mode>

Figure 9:
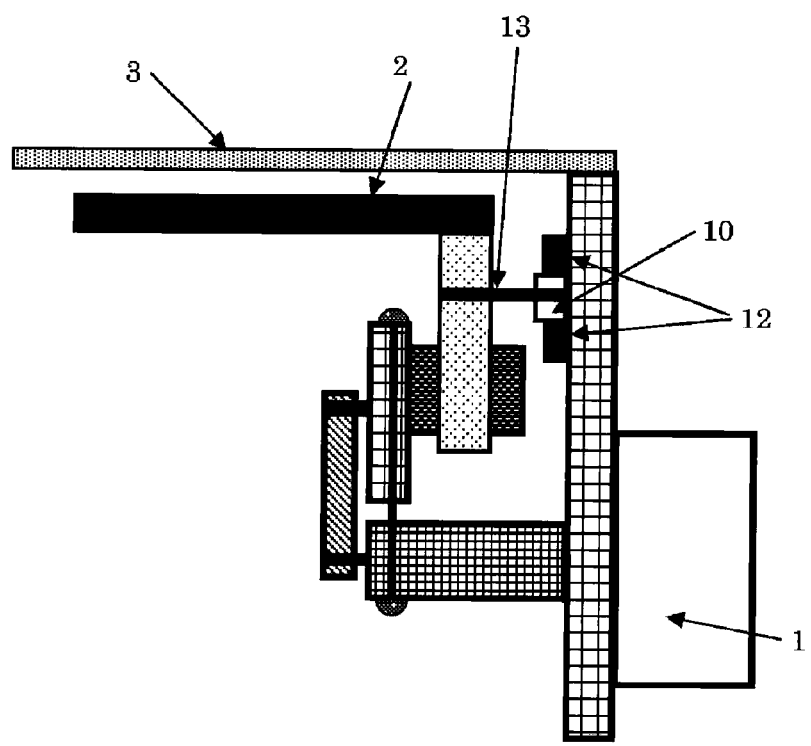
FIG. 9 is a side view of an ultrasonic probe according to a seventh mode of the present invention.

An ultrasonic probe according to a seventh mode of the present invention is illustrated in FIG. 9. The same reference numerals as used in the above modes are employed to describe the corresponding arrangement. Unlike in the sixth mode, the ultrasonic probe of this mode employs an arrangement wherein two guide rails 12 are provided and a roller 10 is located between them, so that a slider shaft, i.e., an ultrasonic element 2 is extended or retracted. Since a phenomenon can be avoided such that the force exerted to press the roller 10 against the guide rails 12 is changed depending on the oscillation position, it is possible to avoid a phenomenon such that a mechanical load imposed on the motor 1 for oscillation is changed, depending on the oscillation angle, and load fluctuation need not be considered when the motor 1 is controlled to perform oscillation. Further, in this mode, one roller is employed for a mechanism section that performs a telescopic movement, the mass of the mechanism section for performing a telescopic movement can be reduced, and vibrations caused by the telescopic movement can be reduced during oscillation. In addition, in a case of wherein the guide rails 12 are formed using machining, grooves can be formed in one milling process, etc., performed along the shapes of the guide rails, and the width of the grooves can be more easily and accurately obtained than are the projected rails for the ultrasonic probe described in the sixth mode.

<Eighth Mode>

Figure 10:
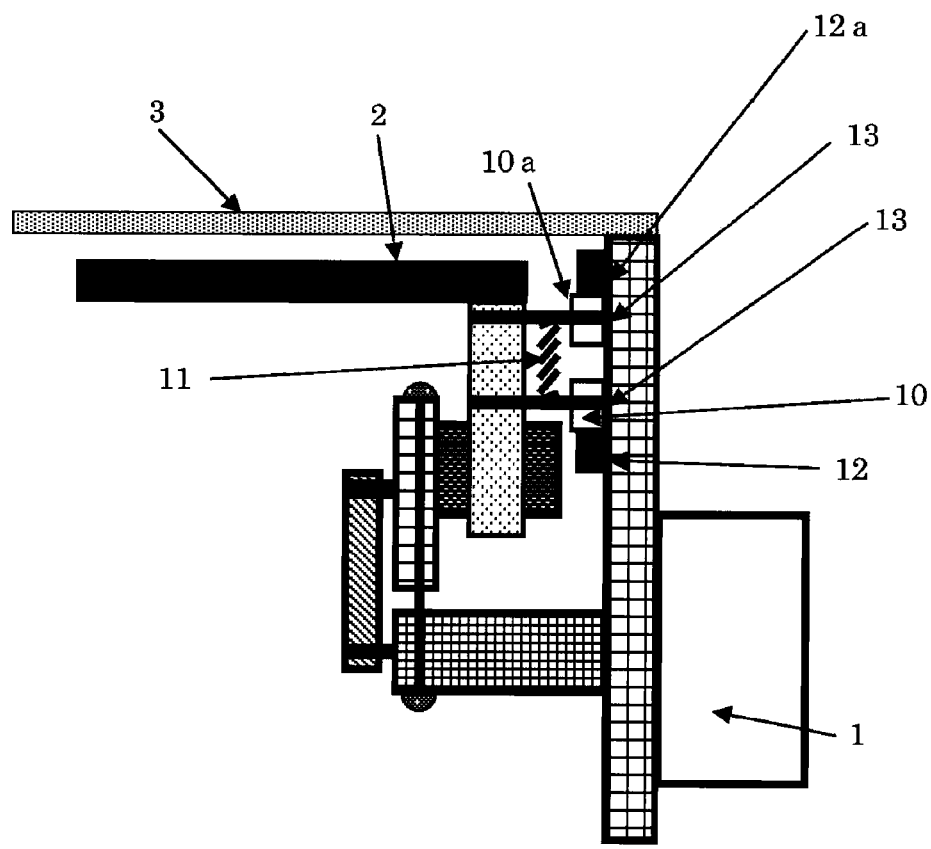
FIG. 10 is a side view of an ultrasonic probe according to an eighth mode of the present invention.

An ultrasonic probe according to an eighth mode of the present invention is illustrated in FIG. 10. The same reference numerals as used in the above modes are employed to describe the corresponding arrangement. According to the ultrasonic probe of this mode, a plurality of rollers 10, 10*a* repel each other, using a spring 11, between a plurality of guide rails 12, 12*a*, and are moved while pressed against the sliding face of the guide rails. With this arrangement, unsteadiness, caused by errors in the groove width of the guide rails and the roller diameter, and load fluctuation can be absorbed by the spring 11. Thus, the motor 1 can be stably and easily controlled when the load fluctuates during oscillation, and the acquisition of a targeted oscillation velocity and a reduction in velocity fluctuation can be provided using a comparatively easy control method.

<Ninth Mode>

Figure 11:
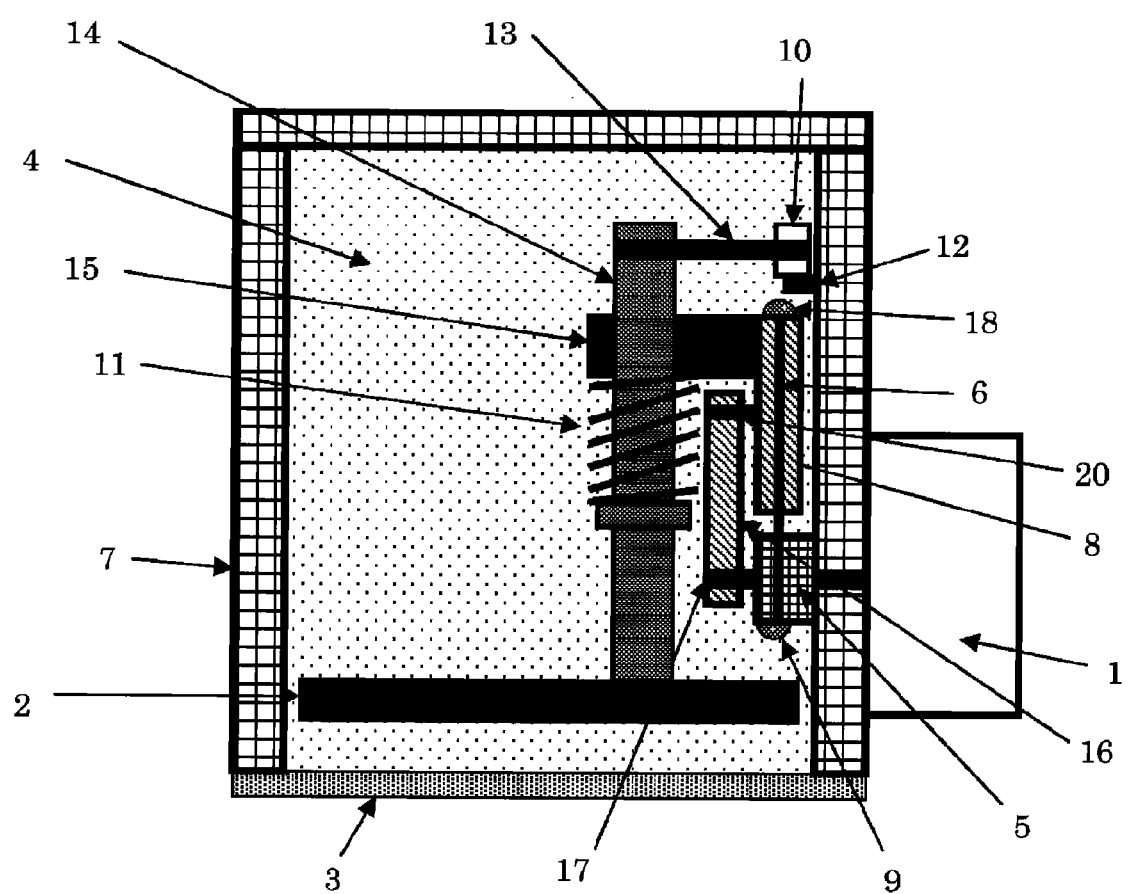
FIG. 11 is a side view of an ultrasonic probe according to a ninth mode of the present invention.
Figure 12:
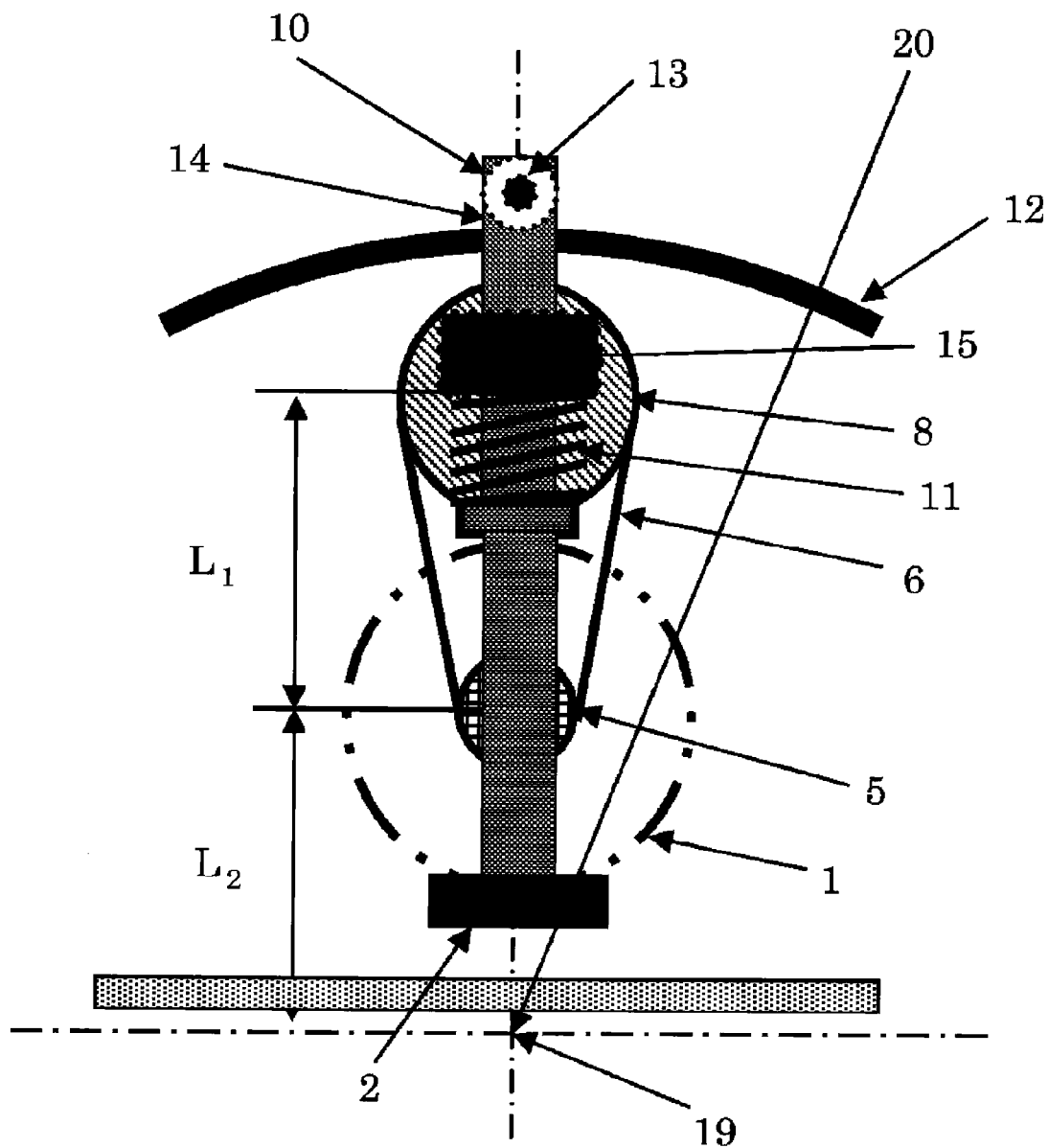
FIG. 12 is a front view of the ultrasonic probe according to the ninth mode of the present invention.

Ultrasonic probes according to the modes of the present invention will now be described while referring to drawings. FIGS. 11 and 12 are a front view and a side view of an ultrasonic probe according to a ninth mode of the present invention. In these drawings, a motor spindle 17 of a motor 1 is to be rotated or oscillated upon externally receiving an electric drive signal from ultrasonic diagnostic equipment (not shown). An ultrasonic element 2 is stored in an area that is enclosed by a window 3 and a probe casing 7, and this area is filled with an acoustic coupling liquid 4 for transferring an ultrasonic signal that is transmitted or received by the ultrasonic element 2.

The motor spindle 17 of the motor 1, which is secured to the outside of the probe casing 7, passes via a sealant, such as material used as an oil seal (not shown), through the probe casing 7 and a first cylinder pulley 5 that is secured to the probe casing 7 and to an arm 16 arranged within the probe casing 7. A pulley shaft 20 is secured to the other end of the arm 16, and a second cylinder pulley 8 is mounted so rotatable around the pulley shaft 20. The first cylinder pulley 5 and the second cylinder pulley 8 are secured using a wire 6 and, respectively, a first wire fastening device 9 and a second wire fastening device 18.

With such an arrangement, wherein the first cylinder pulley 5 and the second cylinder pulley 8 are held by the wire 6, and wherein the first cylinder pulley 5 is secured to the probe casing 7, when the motor spindle 17 rotates and inclines the arm 16, at the same time, the second cylinder pulley 8 begins to be rotated around the pulley shaft 20. Since the slider bearing 15 is secured to the second cylinder pulley 8, the slider bearing 15, as well as the second cylinder pulley 8, is inclined and rotated at the same time as the motor spindle 17 is rotated. The slider shaft 14, slidably attached to the slider bearing 15, also performs the same movements. Further, since the roller 10 that is rotatably attached to the roller shaft 13, which is fixed to the slider shaft 14, is constantly drawn down by the spring 11 to make contact with the guide rail 12, located inside the probe outer case 7, the slider 14, in addition to inclination and rotation, performs a telescopic movement along the shape of the guide rail 12 as the motor spindle 17 is rotated. The ultrasonic element 2 is fixed on the side opposite the end of the slider shaft 14 that is fixed to the roller shaft 13.

At this time, when, as illustrated in FIG. 12, the guide rail 12 is formed in an arced shape that has an a guide rail curvature center 19 as the center, assume that a distance $L_2$ from the guide rail curvature center 19 to the center of the first cylinder pulley 5, i.e., a distance to the center of the motor spindle 17, is set equal to a distance $L_1$ from the center of the first cylinder pulley 5 to the center of the second cylinder pulley 8, and that a ratio of the diameter of the first cylinder pulley 5 to the diameter of the second cylinder pulley 8 is defined as a ratio of one to two.

Figure 13:
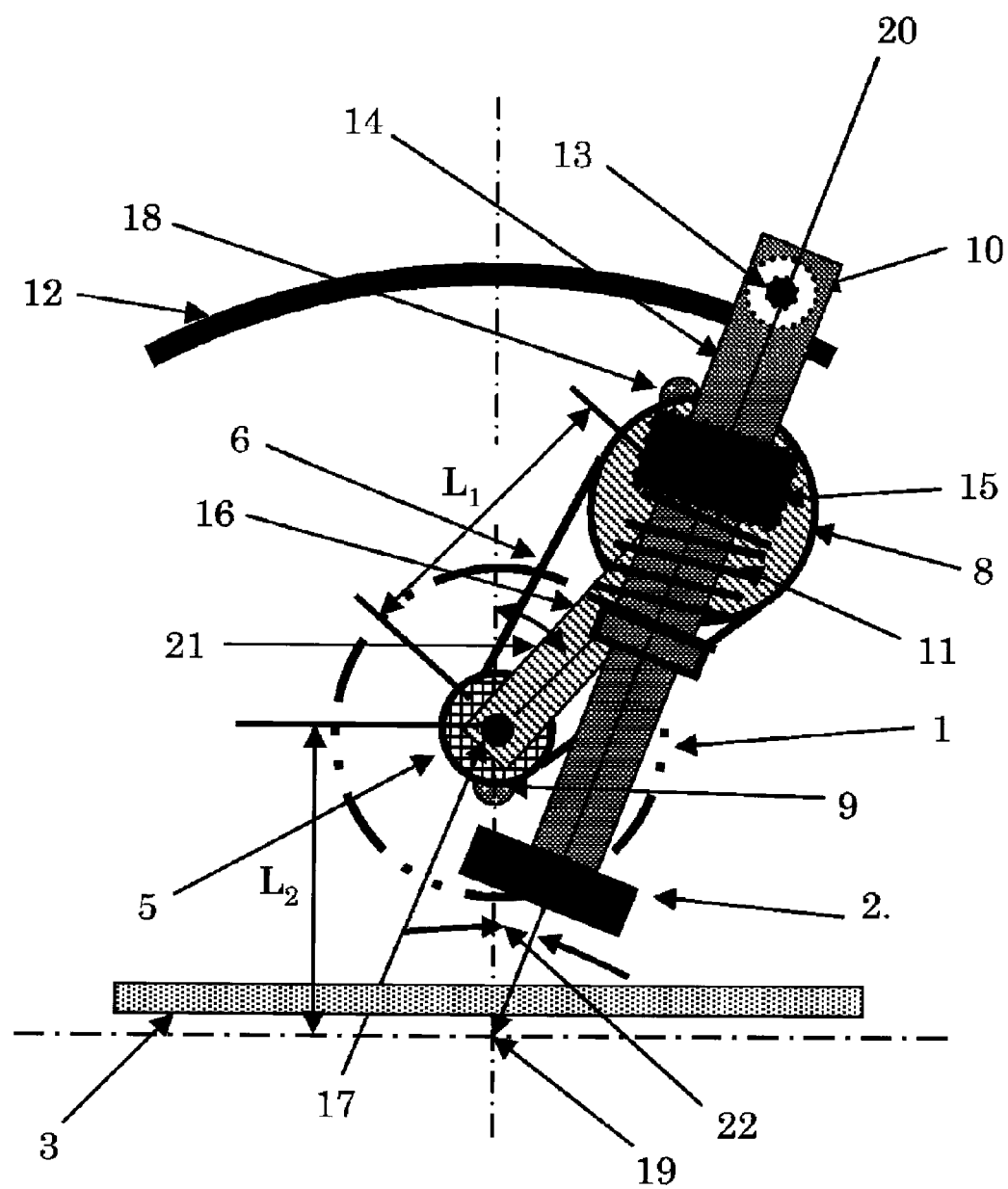
FIG. 13 is a front view for explaining the oscillation state of the ultrasonic probe according to the ninth mode of the present invention.

The state wherein the ultrasonic element 2 is oscillated will now be described in detail while referring to FIG. 13. According to the arrangement of this invention, since the length $L_2$, from the guide rail curvature center 19 to the center of the motor spindle 17, is set equal to the length $L_1$, from the center of the point of the arm 16 secured to the motor spindle 17 to the center of the second cylinder pulley 8, an isosceles triangle is formed by the center of the second cylinder pulley 8, the center of the motor spindle 17 and the guide rail curvature center 19, so that a relationship of two to one is constantly established between a motor spindle rotational angle 21 and an element oscillating angle 22 in FIG. 13. Furthermore, since a ratio of one to two is employed for the diameter of the first cylinder pulley 5 and the diameter of the second cylinder pulley 8, and the first cylinder pulley 5 and the second cylinder pulley 8 are held by a wire or a steel band belt, the second cylinder pulley 8 is rotated, due to the inclination of the arm 16, by ½ a rotation at the pulley shaft 20 in a direction opposite the rotation direction for the motor spindle 17.

Therefore, when the motor spindle 17 is rotated, the slider shaft 14 to which the ultrasonic element 2 is fitted initiates oscillation by employing the guide rail curvature center 19 as the oscillation center, while maintaining a displacement that is ½ the motor spindle rotation angle 21.

Furthermore, the roller 10 is provided for the slider shaft 14 to which the ultrasonic element 2 is secured, so that by means of the spring 11, the roller 10 is constantly held against or brought into contact with the guide rail 12. Thus, while being oscillated from side to side, the ultrasonic element 2 slides relative to the slider bearing 15, and performs a telescopic movement, i.e., the distance from the ultrasonic element 2 to the pulley shaft 20 of the second cylinder pulley 8, to which the slider bearing 15 is fixed, is increased or reduced.

As described above, the ultrasonic element 2 inclines at the guide rail curvature center 19, and also oscillates, due to a telescopic movement, with a large curvature at the guide rail curvature center 19, while a constant distance is maintained from the guide rail curvature center 19.

Further, according to the arrangement of this mode, as the positional relationship wherein the force of the spring is exerted, the roller 10 is drawn toward the guide rail 12 by the spring 11, located between the slider shaft 14 and the slider bearing 15, i.e., the roller 10 is pressed, by the spring 11, against the side of the guide rail 12 opposite the slider bearing side. However, the roller 10 may be provided inside the guide rail 12 (the slider bearing side), and the position of the spring 11 changed to the opposite side, or a compression spring may be exchanged for a tension spring to press against the roller 10. Further, the roller 10 has been made rotatable at the roller shaft 13 in order to reduce sliding resistance. However, a Teflon (registered trademark) resin that has a low sliding resistance may be employed as the material for the guide rail 12 and the roller 10, and the roller 10 need not always be rotatable at the roller shaft 13.

Moreover, as a method for maintaining the roller 10 contact with the guide rail 12, the guide rail may be sandwiched by two or more rollers. As another arrangement, two guide rails 12 may be provided to sandwich the roller in between. In this case, two or more rollers, impelled by springs, may be attached so they repel each other, in order to remove the unsteadiness of the rollers in the grooves of the guide rails. In this case, as for the positional relationship between the center of oscillation, i.e., the guide rail curvature center 19, and the window 3, the oscillation center may be located in front of, or to the rear of, the window 3, in accordance with the diagnosis application.

Further, according to the arrangement described for this mode, the ultrasonic element 2 is oscillated constantly at one point at the center of the inclination angle of the ultrasonic element 2, and the same distance is maintained from the oscillation center to the ultrasonic element 2. However, in a case wherein the center of the oscillation angle need not be the same as the center of the oscillation trajectory, it is not always a requirement that the length from the guide rail curvature center 19 to the center of the motor spindle 17 be equal to the length from the center of the motor spindle 17 to the pulley shaft 20 (the center of the second cylinder pulley 8), and that a ratio for the diameter of the first cylinder pulley 5 to the diameter of the second cylinder pulley 8 be a ratio of one to two.

In addition, the ultrasonic element 2 may be a single element, and the ultrasonic probe may be a mechanical type that employs the above oscillating mechanism to perform mechanical scanning. However, when the ultrasonic element 2 is of an electronic scanning type, or a mechanical scanning structure, to perform mechanical scanning of this invention in a direction perpendicular to the scanning direction, an ultrasonic probe that obtains a three-dimensional ultrasonic image can be provided.

Furthermore, according to the structure illustrated in FIG. 11, the spring 11 is provided as an elastic member between the slider 14 and the slider bearing 15 to press the roller 10 against the contact face of the guide rail 12. In this manner, the roller 10 and the guide rail 12 are pulled together so they always contact each other, and the same interval between the ultrasonic element 2 and the window 3 can be maintained. It should be noted that an elastic member other than a spring can also be employed.

<Tenth Mode>

Figure 14:
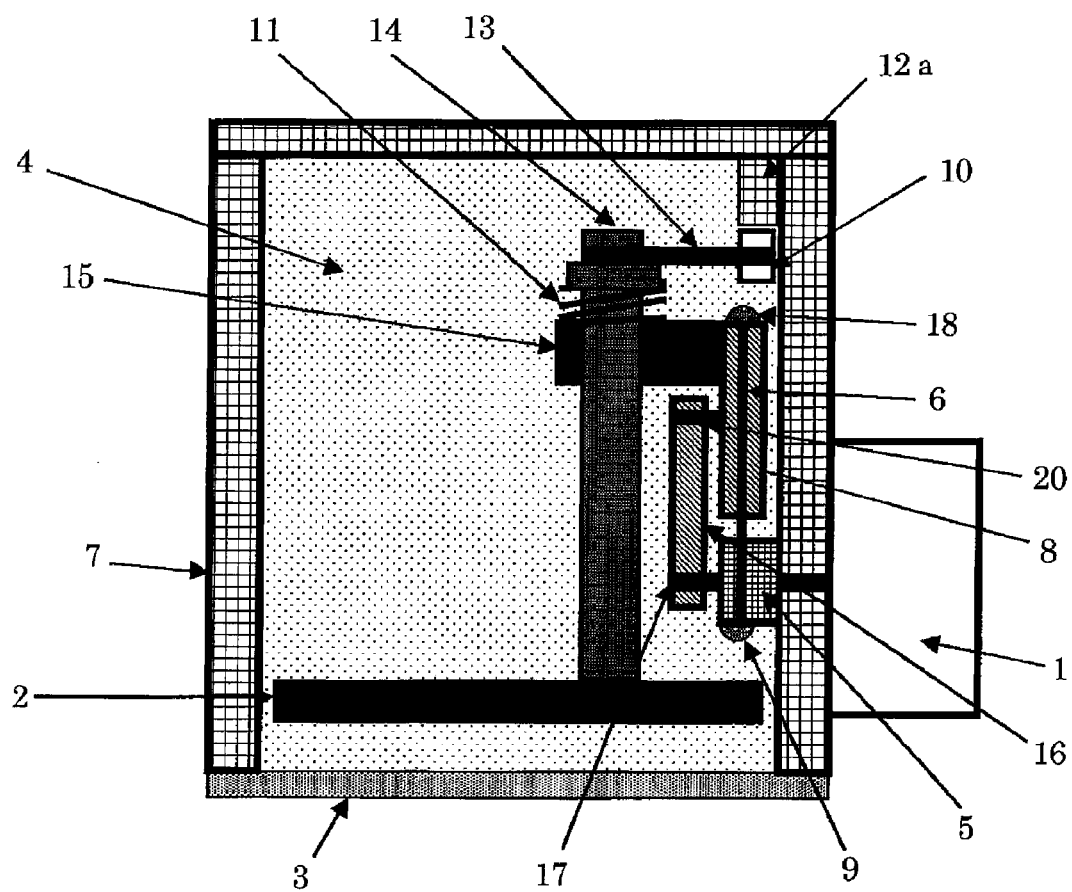
FIG. 14 is a side view of an ultrasonic probe according to a tenth mode of the present invention.

An ultrasonic probe according to a tenth mode of the present invention is illustrated in FIG. 14. The same reference numerals as used in the ninth mode are also employed to describe the corresponding arrangement. In the tenth mode, a point greatly different from the ninth mode is that a guide rail 12a is integrally formed with a probe casing 7. According to this arrangement, since there is no undercut portion, in a case wherein the probe casing 7 is to be formed using a mold, the mold for the probe casing 7 can be raised toward the window 3 after the probe casing 7 has been formed. Therefore, the use of a slider mold is not required, the expenditure for a mold is reduced, and the probe can be manufactured at a low cost. In addition, since a roller 10 is constantly pressed toward the guide rail 12a by a spring 1, a constant distance between an ultrasonic element 2 and the window 3 can be maintained.

<Eleventh Mode>

Figure 15:
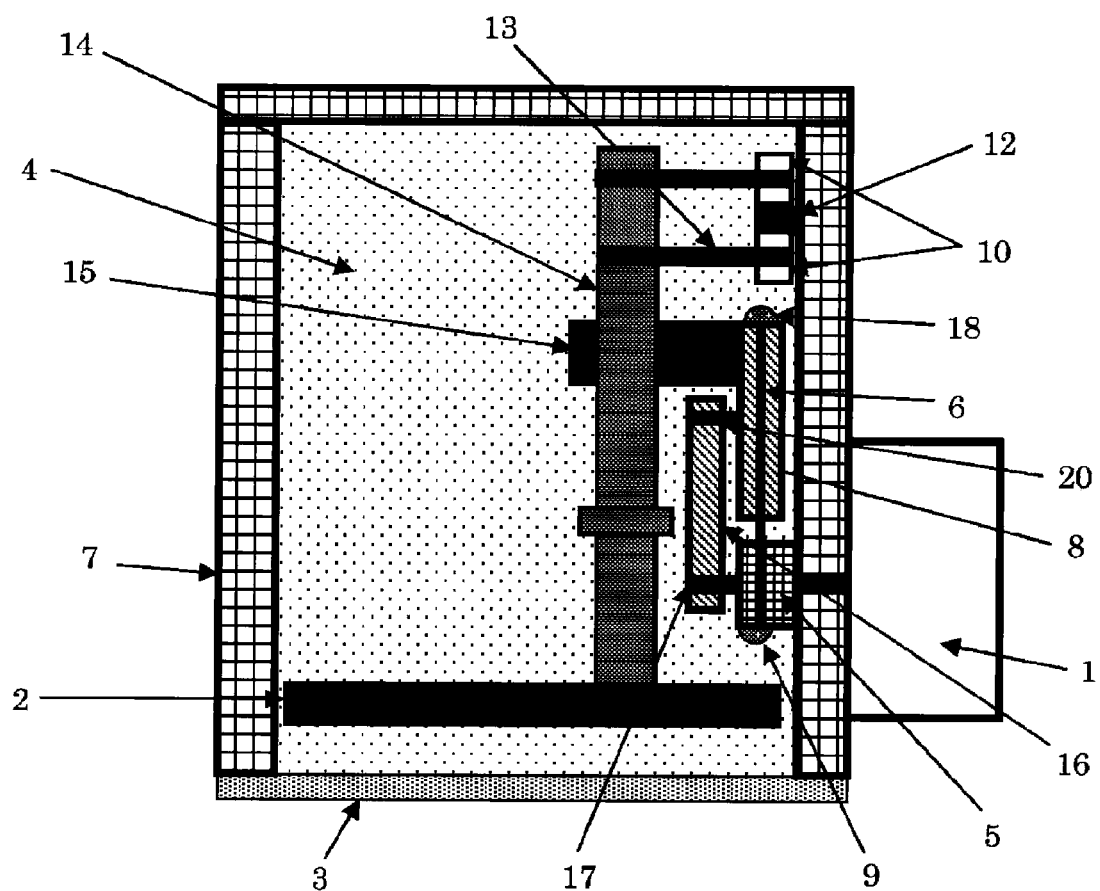
FIG. 15 is a side view of an ultrasonic probe according to an eleventh mode of the present invention.

An ultrasonic probe according to an eleventh mode of the present invention is illustrated in FIG. 15. The same reference numerals as used in the above modes are employed to describe the corresponding arrangement. According to the arrangement of the ultrasonic probe of this mode, a guide rail 12 is arranged so sandwiched between two rollers 10, the spring 11 shown in FIG. 11 is eliminated to always keep the rollers 10 in contact with the guide rail 12, and using these two rollers, the distance between an ultrasonic element 2 and a window 3 is maintained along the guide rail 12. Therefore, it is possible to avoid a phenomenon such that, when the slider shaft 14, i.e., the distance from the slider bearing 15 to the ultrasonic element 2, is extended or retracted by the urging force of the spring 11, the force exerted to press the roller 10 against the guide rail 12 will vary, depending on the oscillation position. Thus, it is also possible to avoid a phenomenon wherein the mechanical load imposed on the motor 1 for oscillation is changed, depending on the oscillation angle, and accordingly, load change need not be considered when the motor 1 for oscillating the ultrasonic element 2 is controlled.

<Twelfth Mode>

Figure 16:
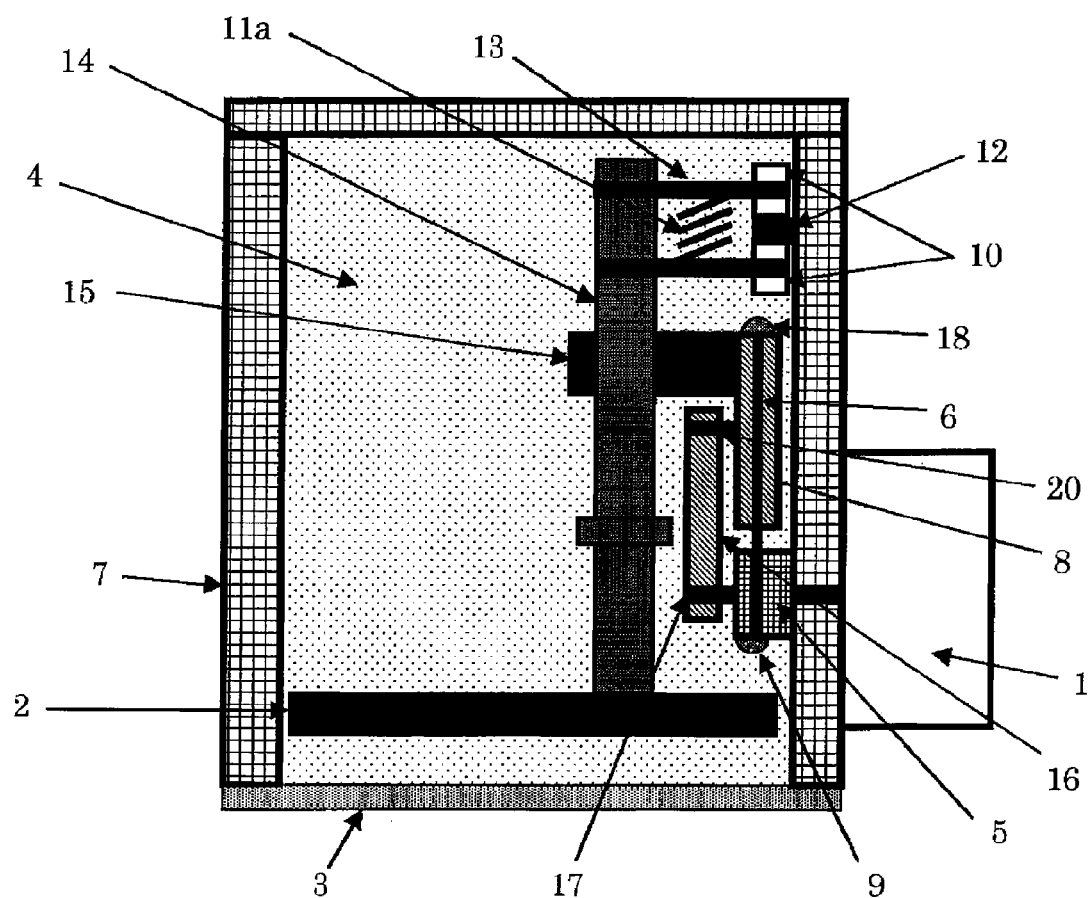
FIG. 16 is a side view of an ultrasonic probe according to a twelfth mode of the present invention.

An ultrasonic probe according to a twelfth mode of the present invention is illustrated in FIG. 16. The same reference numerals as used in the above modes are employed to describe the corresponding arrangement. According to the arrangement of the ultrasonic probe of this mode, a guide rail 12 is sandwiched between two rollers 10, and these two rollers 10, are drawn by a spring 11a. Therefore, since the rollers 10, are drawn in toward each other by the force exerted by the spring 11a, even when the width of the guide rail 12 sandwiched between the two rollers 10, 10a is slightly un-uniform, a load that will be increased in a case where there is a wide guide rail can be reduced, and also, the wobbling that will occur in a case where there is a narrow guide rail can be reduced. It should be noted that, when the rigidity (flexibility) differs between the two roller shafts, wobbling can be prevented by employing one of the roller shafts as a reference, and the positioning accuracy can also be increased.

<Thirteenth Mode>

Figure 17:
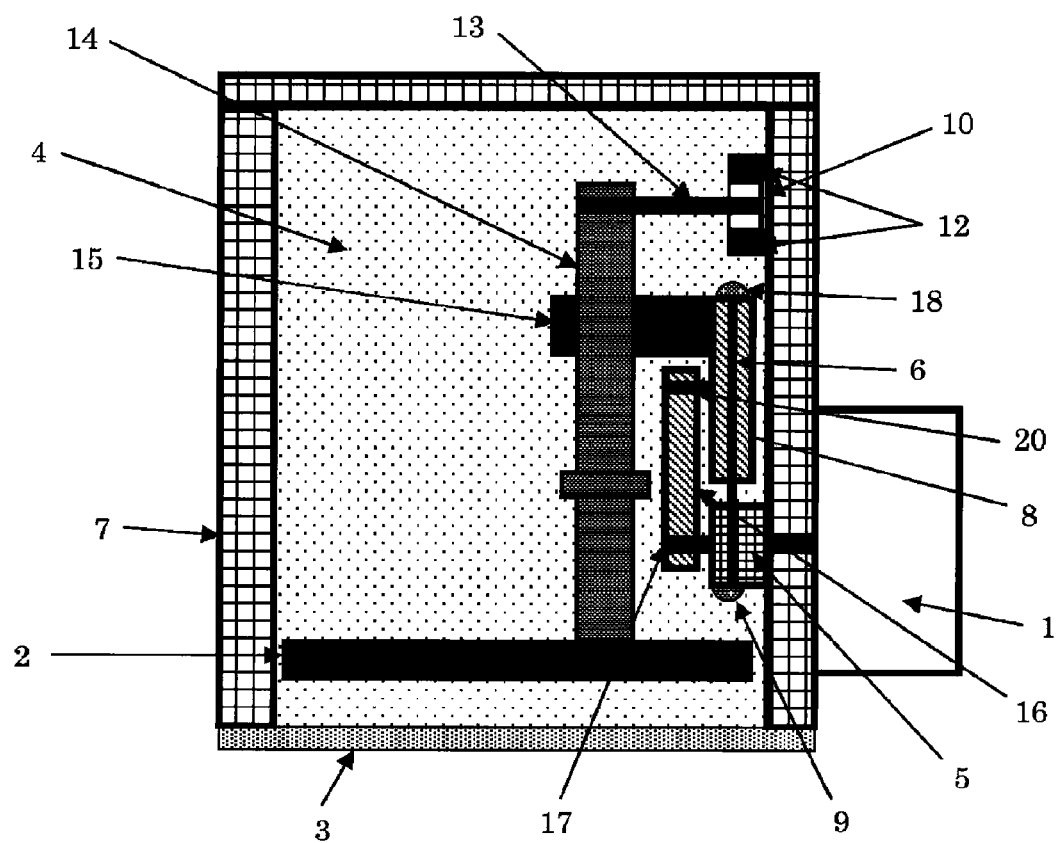
FIG. 17 is a side view of an ultrasonic probe according to a thirteenth mode of the present invention.

An ultrasonic probe according to a thirteenth mode of the present invention is illustrated in FIG. 17. The same reference numerals as used in the above modes are employed to describe the corresponding arrangement. Unlike in the fourth mode, the ultrasonic probe of this mode employs an arrangement wherein two guide rails 12 are provided and a roller 10 is located between them, so that a slider shaft 14, i.e., an ultrasonic element 2 is extended or retracted. Since a phenomenon can be avoided such that the force exerted to press the roller 10 against the guide rails 12 is changed depending on the oscillation position, it is possible to avoid a phenomenon such that a mechanical load imposed on the motor 1 for oscillation is changed, depending on the oscillation angle, and load fluctuation need not be considered when the motor 1 is controlled to perform oscillation. Further, in this mode, one roller is employed for a mechanism section that performs a telescopic movement, the mass of the mechanism section for performing a telescopic movement can be reduced, and vibrations caused by the telescopic movement can be reduced during oscillation. In addition, in a case of wherein the guide rails 12 are formed using machining, grooves can be formed in one milling process, etc., performed along the shapes of the guide rails, and the width of the grooves can be more easily and accurately obtained than are the projected rails.

<Fourteenth Mode>

Figure 18:
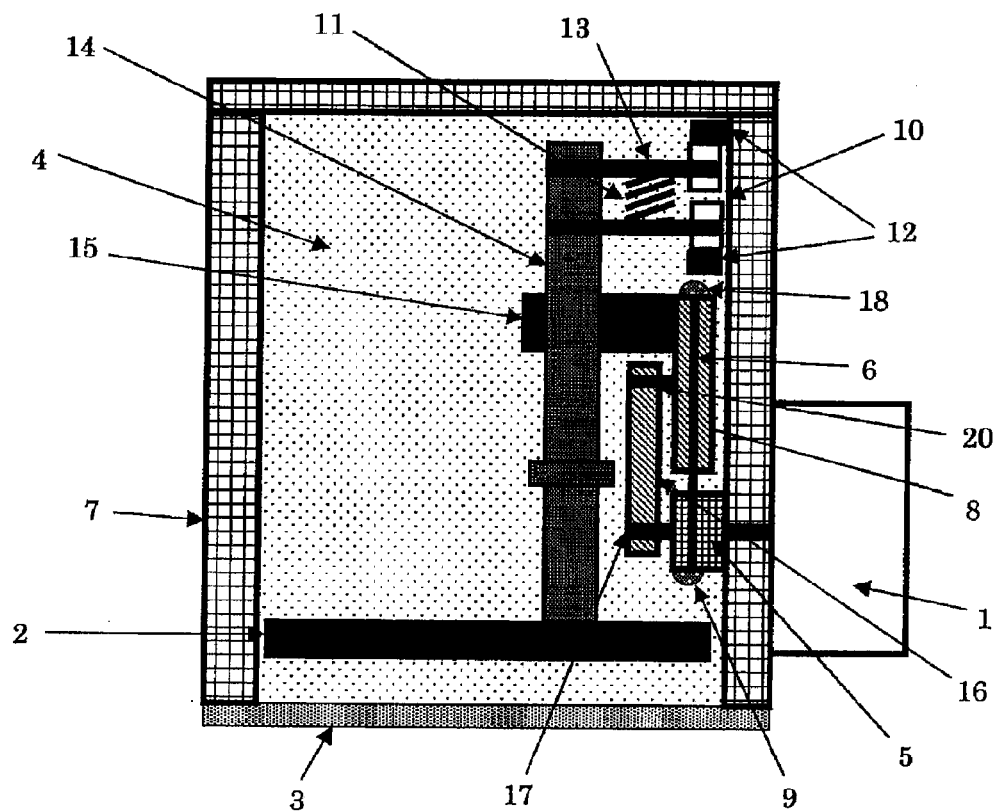
FIG. 18 is a side view of an ultrasonic probe according to a fourteenth mode of the present invention.

An ultrasonic probe according to a fourteenth mode of the present invention is illustrated in FIG. 18. The same reference numerals as used in the above modes are employed to describe the corresponding arrangement. The ultrasonic probe of this mode is an improved proposal for the thirteenth mode; a plurality of rollers 10 repel each other, using a spring 11, between a plurality of guide rails 12, and are moved while pressed against the sliding face of the guide rails. With this arrangement, in addition to the characteristic of the guide rail formation method in the thirteenth mode, unsteadiness, caused by errors in the groove width of the guide rails 12 and the roller 10 diameter, and load fluctuation can be absorbed by the spring 11. Thus, the motor 1 can be stably and easily controlled when the load fluctuates during oscillation, and the acquisition of a targeted oscillation velocity and a reduction in velocity fluctuation can be provided using a comparatively easy control method.

<Fifteenth Mode>

Figure 19A:
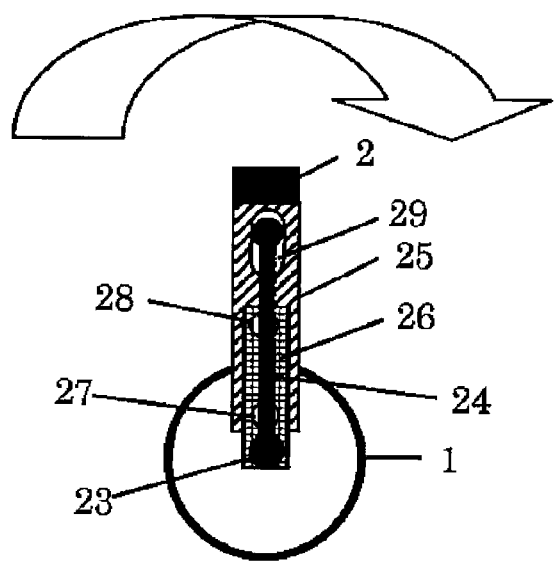
FIG. 19A is a front view for explaining an ultrasonic probe according to a fifteenth mode of the present invention.
Figure 19B:
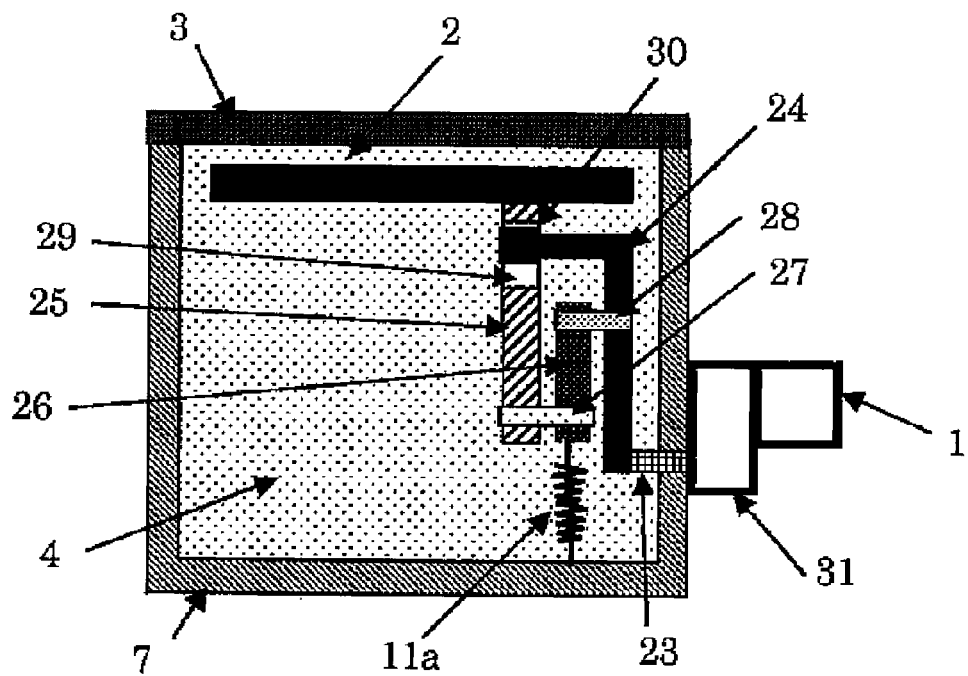
FIG. 19B is a front view for explaining the ultrasonic probe according to the fifteenth mode of the present invention.

FIGS. 19A and 19B are a front view and a side view of an ultrasonic probe according to a fifteenth mode of the present invention. In FIGS. 19A and 19B, a motor spindle 23 is coupled to a motor 1 via a speed reduction mechanism 31, and is to be rotated, or oscillated, upon receiving a drive electric signal from an external apparatus, such as an ultrasonic diagnostic apparatus (not shown). A first arm 24, which is fixed at one end to the motor spindle 23, is to be rotated or oscillated at the motor spindle 23 in accordance with the rotation of the motor spindle 23. Further, a second shaft 28 is rotatably fitted to the longitudinal intermediate portion of the first arm 24, so that the first arm 24 is connected rotatably also to the second shaft 28. And a third arm 26 is rotatably fitted at the other end of the second shaft 28, a first shaft 27 is rotatably fitted to the other end of the second arm 26, and the other end of the first shaft 27 is connected to the end of the second arm 25 to be rotatable. The portion where the second arm 25 and the third arm 26 are rotatably fitted over the first shaft 27 is to be drawn in by a spring 11a toward a probe casing 7. Furthermore, an ultrasonic element 2, for performing conversions for an electric signal and an ultrasonic signal, is fixed at the tip of the other end of the second arm 25. The ultrasonic element 2 is stored in an area enclosed by a window 3 and the probe casing 7, and this area is filled with an acoustic coupling liquid 4 for transferring an ultrasonic signal transmitted by the ultrasonic element 2.

A vertical, long groove portion 29 is formed between the end of the second arm 25 where the ultrasonic element 2 is fixed and the end where the first shaft 27 is secured, and the L-shaped distal end portion of the first arm 24 is fitted on a groove engagement portion 30. The groove portion 29 is a groove that has a width that is substantially equal to the diameter of the L-shaped distal end portion of the first arm 24, and that is vertically extended toward the end where the ultrasonic element is secured and can be moved, parallel, toward the ultrasonic element 2. When the motor spindle 23 is rotated or oscillated, the L-shaped first arm 24 secured to the motor spindle 23 rotates the groove portion 29 of the second arm 25, and accordingly, the ultrasonic element 2 initiates rotation. At this time, a linking mechanism having two rotatable ends is constituted by the third arm 26, together with the first shaft 27 that is provided at the end of the second arm 25, opposite the end where the ultrasonic element is secured, and the second shaft 28 that is provided between the rotational center of the first arm 24 and the groove portion 29 of the second arm 25. Because of this linking mechanism, when the motor spindle 23 is rotated, the ultrasonic element secured end of the second arm 25 is rotated with a rotation radius that is longer than the actual distance relative to the actual motor spindle 23.

Figure 20:
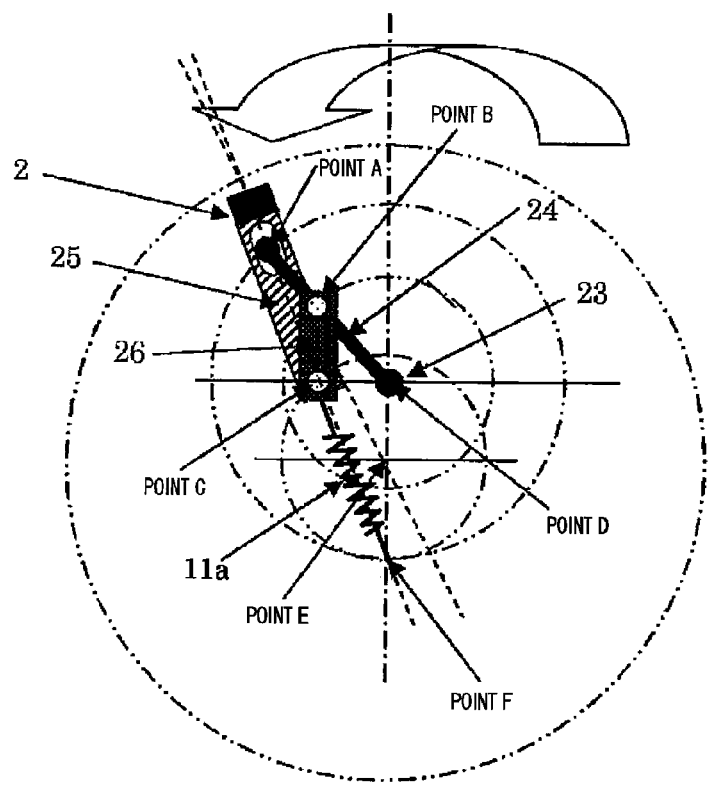
FIG. 20 is a front view for explaining the oscillation state of the ultrasonic probe according to the fifteenth mode of the present invention.

The state wherein the motor spindle 23 is rotated will now be described in detail while referring to FIG. 20. Assuming that the motor spindle 23 is defined as a point D, when the motor spindle 23 is rotated, the first arm 24 secured to the motor spindle 23 is rotated at the point D. When the position of the distal end of the first arm 24 is defined as a point A, the position of the second shaft 28 located between the point A and the motor spindle fixed point is defined as a point B, and the position of the first shaft 27 is defined as a point C, the ultrasonic element 2 is secured to the distal end of the second arm 25, the other end is fitted on the first shaft 27 so rotatable with the third arm 26, and the point A, the point B and the point C always form a triangle. In this arrangement, the first shaft 27 (point C), which is the point where the second arm 25 and the third arm 26 are connected, is to be pulled by the spring 11a from a point F that is located, along the perpendicular line of the motor spindle 23, at a distance equivalent to the length of the first arm 24 extended from the motor spindle 23. In a case wherein the first arm 24 is rotated at the motor spindle 23, the triangular shapes formed by ABC and by ADF are maintained. Therefore, when the first arm 24 is rotated, the point C, i.e., the first shaft 27 draws a circular trajectory, and the distal end of the ultrasonic element 2 also draws a circular trajectory using the point F as the center of the circle. As is apparent from FIG. 20, since the trajectory of the rotation of the ultrasonic element 2 employs the point F as the center, this is equivalent to a case wherein an arm whose rotational center is the point F is rotated. According to this arrangement, the virtual rotational center can be located farther away than the motor spindle 23, viewed from the ultrasonic element 2, and size reduction is enabled, compared with a case wherein the actual rotational center is located at a distance.

That is, when the first arm 24 secured to the point D, which is the position of the motor spindle 23, is rotated at the point D, the second arm 25 is oscillated while the point A that is the distal end position of the first arm 24 is moved parallel along the groove portion 29 formed in the second arm 25. The point C, which is the position of the lower end of the third arm 26 in FIG. 20, is set so that the lower end is rotatable with the lower end of the second arm 25, while the point B, which is the position of the upper end of the third arm 26 in FIG. 20, is set so that the upper end is rotatable between the ends of the first arm 24, and a triangle is formed using the points A, B and C. In this arrangement, when the first arm 24 is rotated, the distal end of the second arm 25 can be oscillated along a trajectory having a larger curvature than when being oscillated at the point D, which is the location of the motor spindle 23.

Further, when the distance from the point A to the point B is equal to the distance from the point B to the point C, and when the length from the point A to the point D is equal to the length from the point D to the point F, the triangle ABC and the triangle ADF are always similar isosceles triangles. When the triangles ABC and ADF are isosceles triangles, the rotation angle of the ultrasonic element 2 is always inclined ½ the rotation angle of the first arm 24. Thus, the relationship two to one is consistently established between the oscillating angle of the ultrasonic element 2 and the rotational angle of the motor 1, and when a predetermined rotational angle for the motor is employed for oscillation, the rotational angle for the ultrasonic element 2 can also be uniform, consistently, by using the point F as the center.

Specifically, the point B, which is the position of the second shaft 28 along the first arm 24, is secured to provide the same length for line segments A-B and B-C and the same length for line segments A-D and D-F, and isosceles triangles ABC and ADF are formed. In this arrangement, when the first arm 24 is rotated, the triangles ABC and ADF are always isosceles triangles, and the isosceles triangle ADF is similar to the triangle ABC. With this arrangement, when the first arm 24 is rotated at an angle θ, the distal end of the second arm 25 is rotated at an angle of (½)θ at a virtual rotational center point E. That is, the same oscillating angle as for the oscillation at the point F, using a long arm, can be provided by using a short arm.

Furthermore, a point where the first arm 24 and the third arm 26 are coupled, i.e., the center axis position of the second shaft 28, which connects these arms, is near the sliding point, in the middle between the point on the first arm 24 where the motor spindle 23 is secured and the sliding point on the second arm 25. Furthermore, the isosceles triangle ABC is provided. With this arrangement, oscillation equal to ½ the rotational angle of the motor 1 is maintained, and during the oscillation, the travel distance for the point C, which is the point at which the second arm 25 and the third arm 26 are coupled, can be decreased in the vertical direction in FIG. 20, and the area wherein the point C descends can be reduced at the maximum oscillation angle. As a result, downsizing is enabled.

That is, the point B, at which the first arm 24 and the third arm 26 are rotatably connected, is located nearer the point A, from the position half the distance between the point D, which is the point on the first arm 24 at which the motor spindle 23 is secured, and the point A, which is the position at the distal end of the first arm 24. Thus, when the first arm 24 is oscillated, the distance the point C projects downward from point D of the motor spindle 23 can be reduced, and the size of the scanning mechanism that oscillates the ultrasonic element 2 can be reduced.

In other words, the length of the third arm 26, from the coupling point for the first arm 24 to the coupling point for the second arm 25, is equal to the length of the first arm 24, from the coupling point for the third arm 26 to the coupling point for the second arm 25. Further, the spring 11a is located at an intersection point between the motor-shaft perpendicular line, with the trajectory of the distal end of the first arm 24 on the side opposite the end where the ultrasonic element 2 is secured, and the end portion at which the second arm 25 and the third arm 26 are connected using the first shaft 27. And the triangle formed using the individual coupling points is an isosceles triangle. With this arrangement, the scanning mechanism that oscillates the ultrasonic element 2 can more compactly be constructed.

In addition, since the speed reduction mechanism 31 is provided for the motor spindle 23, it is natural that a torque consonant with the load imposed on the oscillation mechanism can be provided by a small motor. Furthermore, the oscillation angle of the ultrasonic element 2 can be controlled and limited to small pitches. In a case wherein the ultrasonic element 2 is to be oscillated at an oscillation angle of ±30 degrees, this corresponds to a shaft rotational angle of ±60 degrees, in accordance with the isosceles triangle ABC. In addition, since the speed reduction mechanism 31 having a ratio of one to six is located in the middle of the rotational centers of the motor spindle 23 and the first arm 24, the oscillation angle of ±30 degrees for the ultrasonic element 2 can be changed to the motor rotational angle of ±360 degrees, and deterioration of the service life due to deviated abrasion of the commutator of a brush motor can be suppressed. Moreover, in a case wherein a pulse motor is employed, since the step angle of a pulse motor affects the fine positioning accuracy required for the oscillating angle of the ultrasonic element 2, a pulse motor controlled by an expensive control circuit, such as a micro-step driving circuit, is required. However, when the above described linking mechanism and the speed reduction mechanism 31 are employed together, fine oscillating angle control can be provided by using an inexpensive pulse motor having a wide step angle, a control circuit, and a comparatively small and inexpensive speed reduction mechanism.

That is, instead of directly connecting the rotational center point D of the first arm 24 to the motor spindle 23, a shaft for which the speed is reduced by a speed reduction mechanism 31, such as a gear box or a timing pulley, is connected to the motor spindle 23. With this arrangement, the rotation of the motor is controlled at a rotation angle that is much larger than the oscillating angle of the ultrasonic element 2. And in a case wherein the oscillation is controlled using a pulse motor having a large pitch, or using a DC motor and an encoder, the position of the element portion can be controlled more precisely using, for example, an encoder having a large pitch.

In addition, the ultrasonic element 2 may be a single element, and the ultrasonic probe may be a mechanical type that employs the above oscillating mechanism to perform mechanical scanning. However, when the ultrasonic element 2 of an electronic scanning type is arranged to perform electronic scanning in a direction perpendicular to the mechanical oscillation direction, an ultrasonic probe can be provided that performs electronic scanning and mechanical scanning and obtains a three-dimensional ultrasonic image.

That is, the ultrasonic element 2 is an electronic scanning element, and when electronic scanning is performed in a direction perpendicular to the direction of the scanning performed using mechanical oscillation, the ultrasonic probe is provided that enables three-dimensional scanning by performing both electronic scanning and mechanical scanning.

<Sixteenth Mode>

Figure 21A:
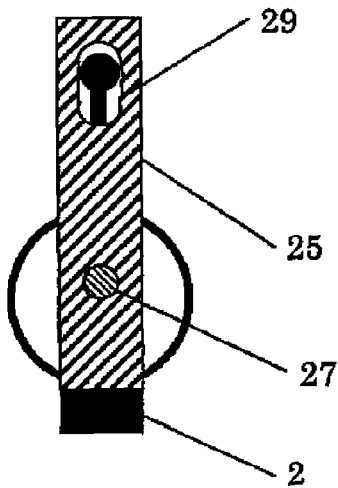
FIG. 21A is a front view for explaining an ultrasonic probe according to a sixteenth mode of the preset invention, with a probe casing removed.
Figure 21B:
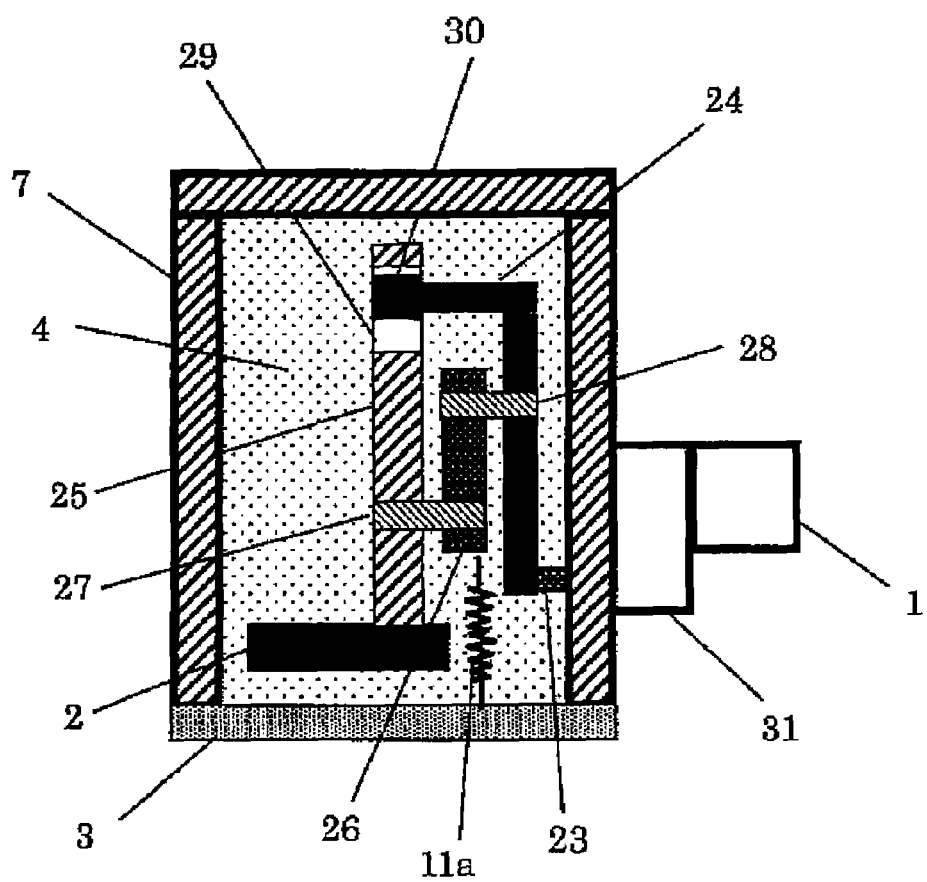
FIG. 21B is a cross-sectional view for explaining the ultrasonic probe according to a sixteenth mode of the preset invention, taken from the side that includes the probe casing.

FIGS. 21A and 21B are a front view of an ultrasonic probe, according to a sixteenth mode of the preset invention, from which a probe casing has been removed, and a cross-sectional side view that includes the probe casing. In FIGS. 21A and 21B, a motor spindle 23 is passed through a probe casing 7 and is connected to a motor 1 via a speed reduction mechanism 31, and upon receiving an electric drive signal from the outside unit, such as the main body of an ultrasonic diagnostic apparatus (not shown), the motor spindle 23 is rotated or oscillated, within an arbitrarily designated range, in an acoustic coupling liquid 4 sealed in the probe casing 7 by an oil seal (not shown) and a window 3.

When the motor spindle 23 is rotated or oscillated, a first arm 24, the base end of which is secured to the motor spindle 23, is rotated or oscillated at the motor spindle 23. Further, a second shaft 28 is rotatably fitted to the longitudinal, intermediate portion of the first arm 24, and one end of a third arm 26 is rotatably connected to the second shaft 28. A first shaft 27 is rotatably fitted on the other end of the third arm 26, and the longitudinal intermediate portion of the second arm 25 is rotatably connected to the first shaft 27. The portion where the second arm 25 and the third arm 26 are rotatably coupled by the first shaft 27 is drawn, by a spring 11a, toward the end of the second arm 25, where an ultrasonic element is secured. An ultrasonic element 2 for performing conversions for an electric signal and an ultrasonic signal is secured to the distal end of the second arm 25, along a line extended from the first shaft 27, i.e., on the window 3 side.

The first arm 24, the second arm 25 and the third arm 26 are connected rotatably using the first shaft 27 and the second shaft 28, and so long as one end of a shaft is fixed to one of these arms and the other end is rotatable, the above described arrangement need not always be employed. A vertical, long groove portion 29 is formed at the end of the second arm 25, opposite the ultrasonic element fixed end of the portion where the first shaft 27 is fixed, and an L-shaped groove engagement portion 30, at the distal end of the first arm 24, is fitted in the groove portion 29. The groove engagement portion 30 of the first arm 24 need not be a L-shaped portion that is integrally formed with the arm, and a separate shaft may be fixed to the arm to be provided as the groove engagement portion 30. The groove portion 29 is a vertical, long groove extended in the longitudinal direction of the second arm 25, that has substantially the same width as the diameter of the L-shaped distal end of the first arm 24, and that can be moved in parallel. Furthermore, as little wobbling as possible in the widthwise direction is preferable in order to increase the response and the positional accuracy of the ultrasonic element.

When the motor shaft 23 is rotated, the first L-shaped arm 24, whose base end is fixed to the motor shaft 23, initiates rotation of the groove portion 29 of the second arm 25, and thus, the ultrasonic element 2 begins to rotate. At this time of rotation, the ultrasonic element 2, fixed to the second arm 25 on the window 3 side, employs the window vicinity as the virtual oscillation center. For the groove engagement portion, a bearing or a low friction-resistant resin material may be provided to reduce a sliding friction resistance. Further, here, the arrangement wherein the groove engagement portion 30 is fitted into the groove portion 29 formed in the second arm 25 is employed as an example; however, the second arm 25 may be sandwiched by two or more bearings.

Figure 22:
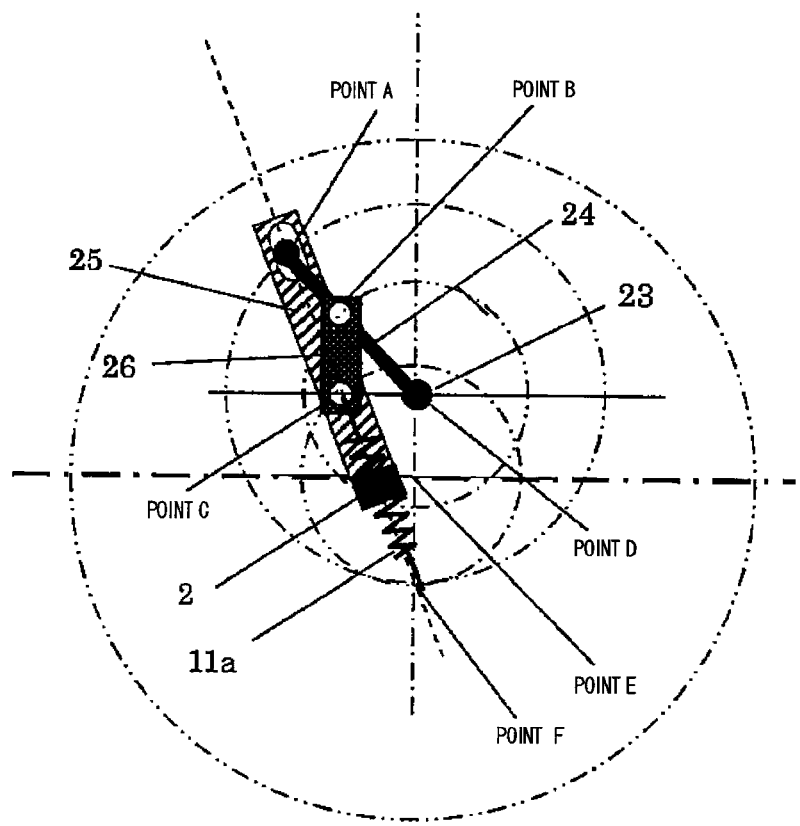
FIG. 22 is a schematic diagram for explaining the oscillation state of the ultrasonic probe according to the sixteenth mode of the present invention.

The state wherein the motor shaft 23 is rotated will now be described in detail while referring to FIG. 22. FIG. 22 is a schematic diagram illustrating shorter arms nearer the front, in order for the positional relationship of the arms to be understood. Assuming that the motor shaft 23 is at a point D, when the motor shaft 23 is rotated, the first arm 24 secured to the motor shaft 23 is rotated at the point D. Assuming that the position of the distal end of the first arm 24 is a point A, the position of the second shaft 28, between the point A and the motor shaft fixed point, is a point B, and the point where the first shaft 27 is secured is a point C, the ultrasonic element 2 is fixed to the window 3 end of the second arm 25, and the third arm 26 is secured, by the first shaft 27, between the ultrasonic-element secured end of the second arm 25 and the point A. And, at a position other than the position where the individual arms linearly overlap, a triangle is always formed by the points A, B and C.

At this time, the arrangement in FIG. 22 is employed, wherein the first shaft 27 (point C), which is the coupling point for the second arm 25 and the third arm 26, is drawn toward the point F, by the spring 11a, at a distance equivalent to the length of the first arm 24, which is extended downward, from the motor shaft 23, along a perpendicular line (a line that matches the vertical direction in FIG. 22) that is perpendicular to the direction toward the motor shaft 23. In a case wherein the first arm 24 is rotated at the motor shaft 23, the points A, B and C and the points A, D and F still form triangles. Therefore, when the first arm 24 is rotated, the distal end of the ultrasonic element 2 draws the oscillation trajectory at the point F drawn by the spring 11a. As is apparent from FIG. 22, since the trajectory of the rotation of the ultrasonic element 2 is drawn at point F, the area in the vicinity of the window can be employed for oscillation, while the virtual rotational center is arranged farther away than the actual rotation center of the motor.

That is, when the first arm 24 secured to the point D, which is the position of the motor spindle 23, is rotated at the point D, the second arm 25 is oscillated while the point A that is the distal end position of the first arm 24 is moved parallel along the groove portion 29 formed in the second arm 25. The point C, which is the position of the lower end of the third arm 26 in FIG. 22, is set so that the lower end is rotatable with the lower end of the second arm 25, while the point B, which is the position of the upper end of the third arm 26 in FIG. 22, is set so that the upper end is rotatable between the ends of the first arm 24, and a triangle is formed using the points A, B and C. In this arrangement, when the first arm 24 is rotated, the distal end of the second arm 25 can be oscillated along a trajectory at the point F that is located near the window.

Further, when the distance from the point A to the point B is equal to the distance from the point B to the point C, and when the length from the point A to the point D is equal to the length from the point D to the point F, the triangle ABC and the triangle ADF are always similar isosceles triangles. When the triangles ABC and ADF are isosceles triangles, the rotation angle of the ultrasonic element 2 is always inclined ½ the rotation angle of the first arm 24. Thus, the relationship two to one is consistently established between the oscillating angle of the ultrasonic element 2 and the rotational angle of the motor 1, and when a predetermined rotational angle for the motor for the unit hour is employed for oscillation, the rotational angle for the ultrasonic element 2 can also be consistently uniform, during the unit hour, by using the point F as the center.

Specifically, the point B, which is the position of the second shaft 28 along the first arm 24, is secured to provide the same length for line segments A-B and B-C and the same length for line segments A-D and D-F, and isosceles triangles ABC and ADF are formed. In this arrangement, when the first arm 24 is rotated, the triangles ABC and ADF are always isosceles triangles, and the isosceles triangle ADF is similar to the triangle ABC. With this arrangement, when the first arm 24 is rotated at an angle θ, the distal end of the second arm 25 is rotated at an angle of (½)θ at a virtual rotational center point E. That is, oscillation can be performed at the vicinity of the window, while ½ of the motor rotation angle is consistently maintained.

An arrangement can be provided such that the ultrasonic element 2, fixed to the second arm 25, is oscillated in the window 3 of the ultrasonic probe, and that the oscillation center of the ultrasonic element 2 is located near the window 3.

That is, the point B, at which the first arm 24 and the third arm 26 are rotatably connected, is located nearer the point A, from the position half the distance between the point D, which is the point on the first arm 24 at which the motor spindle 23 is secured, and the point A, which is the position at the distal end of the first arm 24. Thus, when the first arm 24 is oscillated, the distance the point C projects downward from point D of the motor spindle 23 can be reduced, and the size of the scanning mechanism that oscillates the ultrasonic element 2 can be reduced. And a scanning mechanism that oscillates the ultrasonic element 2 can be made more compactly, and the oscillating mechanism can be located inside the window of the ultrasonic probe to perform scanning at a large oscillation angle.

In other words, the length of the third arm 26, from the coupling point for the first arm 24 to the coupling point for the second arm 25, is equal to the length of the first arm 24, from the coupling point for the third arm 26 to the coupling point for the second arm 25. Further, the spring 11a is located at an intersection point between the motor-shaft perpendicular line, with the trajectory of the distal end of the first arm 24 on the side opposite the end where the ultrasonic element 2 is secured, and the end portion at which the second arm 25 and the third arm 26 are connected using the first shaft 27. And the triangle formed using the individual coupling points is an isosceles triangle. With this arrangement, the scanning mechanism that oscillates the ultrasonic element 2 can more compactly be constructed. At the same time, the oscillation scanning can be performed, while the relationship of two to one is maintained for the rotational angle of the motor and the oscillation angle of the ultrasonic element.

In addition, since the speed reduction mechanism 31 is employed for the motor spindle 23 to fix to the first arm 24 the output shaft of the speed reduction mechanism 31, it is natural that a torque consonant with the load imposed on the oscillation mechanism can be provided by a small motor. Furthermore, the oscillation angle of the ultrasonic element 2 can be controlled and limited to small pitches. In a case wherein the ultrasonic element 2 is to be oscillated at an oscillation angle of ±30 degrees, this corresponds to a shaft rotational angle of ±60 degrees, in accordance with the isosceles triangle ABC. In addition, since the speed reduction mechanism 31 having a ratio of one to six is located in the middle of the rotational centers of the motor spindle 23 and the first arm 24, the oscillation angle of ±30 degrees for the ultrasonic element 2 can be changed to the motor rotational angle of ±360 degrees, and deterioration of the service life due to deviated abrasion of the commutator of a brush motor can be suppressed. Moreover, in a case wherein a pulse motor is employed, since the step angle of a pulse motor affects the fine positioning accuracy required for the oscillating angle of the ultrasonic element 2, a pulse motor controlled by an expensive control circuit, such as a micro-step driving circuit, is required. However, when the above described linking mechanism and the speed reduction mechanism 31 are employed together, fine oscillating angle control can be provided by using an inexpensive pulse motor having a wide step angle, a control circuit, and a comparatively small and inexpensive speed reduction mechanism. Furthermore, since the speed reduction mechanism 31 is provided, the portion where the motor is projected from the oscillation mechanism toward the window 3 can be reduced in size, and the size of the body contact portion of the ultrasonic probe, as well as the size of the ultrasonic probe itself, can be reduced.

That is, instead of directly connecting the rotational center point D of the first arm 24 to the motor spindle 23, a shaft for which the speed is reduced by a speed reduction mechanism 31, such as a gear box or a timing pulley, is connected to the motor spindle 23. With this arrangement, the rotation of the motor is controlled at a rotation angle that is much larger than the oscillating angle of the ultrasonic element 2. And in a case wherein the oscillation is controlled using a pulse motor having a large pitch, or using a DC motor and an encoder, the position of the element portion can be controlled more precisely using, for example, an encoder having a large pitch.

In addition, the ultrasonic element 2 may be a single element, and the ultrasonic probe may be a mechanical type that employs the speed reduction mechanism 31 to perform mechanical scanning. However, when the ultrasonic element 2 is arranged as a mechanical scanning ultrasonic probe that includes an independent mechanism for mechanically rotating or oscillating, or as an ultrasonic element of an electronic scanning type that performs mechanical or electronic scanning in a direction perpendicular to the mechanical oscillation direction, an ultrasonic probe that can obtain a three-dimensional ultrasonic image can be provided.

That is, the ultrasonic element 2 is an electronic scanning element, and when electronic scanning is performed in a direction perpendicular to the direction of the scanning performed using mechanical oscillation, the ultrasonic probe is provided that enables three-dimensional scanning by performing both electronic scanning and mechanical scanning.

As described above, according to the present invention, a triangular linking mechanism is constituted by: the first arm 24, which is secured, so rotatable, at the motor shaft 23; the second arm 25, to which the L-shaped distal end of the first arm 24, opposite the secured motor-shaft end, is fitted so as to be shifted in parallel in the longitudinal direction; and the third arm 26, which is attached, so rotatable, to both the first shaft 27, which is secured between the portion of the second arm 25 where the first arm 24 is fitted and the window 3 side end where the ultrasonic element 2 is secured, and the second shaft 28, which is secured between the secured motor end of the first arm 24 and the L-shaped engagement portion. The portion where the second arm 25 and the third arm 26 are rotatably connected by the first shaft 27 is drawn, by the spring 11a, toward the end of the second arm 25, to which ultrasonic element 2 is secured. According to this simple arrangement, when the motor 1 is rotated, for scanning, the ultrasonic element 2 can be mechanically oscillated along the trajectory that is drawn in the vicinity of the window 3 that contacts an organism. When the center point of the sector radiation of the ultrasonic element 2 is set near the window, obstacles along the ultrasonic transmission/reception path can be avoided for scanning. Therefore, a small, light and inexpensive ultrasonic probe can be provided that is appropriate for sector scanning via a narrow organ contacting area, such as a gap between the ribs or the anterior fontanelle, or for scanning the heart, etc., from the lower edge of the costal arch, i.e., from below the ribs.

In addition, the length of the third arm 26, from the center of the first shaft 27 to the center of the second shaft 28, is set equal to the length from the second shaft 28 to the coupling point of the first arm 24 and the second arm 25, and an isosceles triangle is formed by the individual coupling points for the first arm 24 and the second arm 25. Furthermore, the distance between the motor shaft fixed end 2 of the first arm 24 and the second arm 25 is set so equal to the distance between the motor shaft 23 and the point F, where the spring 11a is secured to the lower portion in the drawing, along the perpendicular motor shaft line. In this manner, an isosceles triangle is formed by the individual points, and with this arrangement, the relationship of two to one is always established between the rotation angle of the motor and the oscillation angle of the ultrasonic element, and the angular rotational speed of the motor is a constant. Thus, the ultrasonic beam can be transmitted and received at the same intervals along the time axis, and the density of the acoustic scanning lines can be maintained.

Furthermore, the coupling point for the first arm 24 and the third arm 26 is located nearer the distal end from the rotation center of the first arm 24, i.e., from the middle of the motor shaft secured point and the distal end of the first arm 24. As a result, the linking mechanism can be downsized, and the reduction in the size and the weight that is requested for the hand-held ultrasonic probe can be provided.

Furthermore, the speed reduction mechanism 31, such as a speed reduction gear, a timing belt or a steel band belt, is mounted on the motor shaft 23, the rotational center of the first arm 24, for oscillation, is secured to the rotary shaft, the speed of which is reduced, and the motor 1 is arranged separate from the window 3. Thus, oscillation can be enabled using a small, light motor, and at the same time, a small body surface contacting portion, i.e., the window portion, can be employed. As a result, an ultrasonic probe can be obtained that is appropriate for scanning via a narrow organism contacting area.

Moreover, when the ultrasonic element 2 is a single element that, to perform mechanical scanning, is mechanically rotated or oscillated independently, or when the ultrasonic element 2 is an ultrasonic element of an electronic scanning type, the linking mechanism of this invention can be employed for scanning in a direction perpendicular to the electronic scanning. Thus, a three-dimensional ultrasonic probe can be provided that transmits or receives an ultrasonic beam via a narrow area.

Industrial Applicability

The present invention provides the effects required of a mechanism that can acquire an ultrasonic tomogram by mechanically oscillating an ultrasonic element and that has a large curvature radius that makes it easy for the organism contact portion of a probe to closely contact an organism along the shape of the contact portion. Further, in order to improve the usability of a hand-held ultrasonic probe, the present invention can provide a compact ultrasonic probe that can be applied either for a mechanical ultrasonic probe or for a three-dimensional ultrasonic probe.

Furthermore, the present invention can be employed for a probe that mechanically oscillates an ultrasonic element to obtain an ultrasonic tomogram, and that can perform sector scanning, such as scanning between bones such as the ribs or the anterior fontanelle, to perform a diagnosis for an organism, e.g., a mechanical scanning ultrasonic probe, or a three-dimensional ultrasonic probe that emits an ultrasonic beam via a narrow area in the vicinity of an organism contacting portion.

The invention claimed is:

1. An ultrasonic probe comprising:
a probe casing;
a window which is provided on the probe casing, wherein an acoustic coupling fluid is enclosed in an area defined by the window and the probe casing;
an ultrasonic element which is arranged in the area defined by the window and the casing;
a motor which is secured to an outside of the probe casing, the motor including a motor spindle extending from the motor into the probe casing;
a first cylinder pulley which is secured to an inner wall of the probe casing, the first cylinder pulley having a through-hole, wherein the motor spindle penetrates the through-hole to project from the first cylinder pulley into an interior of the probe casing;
an arm which has a first end that is directly secured to a portion of the motor spindle that penetrates through and projects from the first cylinder pulley, wherein a longitudinal direction of the arm extends perpendicularly with respect to a projecting direction of the motor spindle;
a pulley shaft which is directly secured to a second end of the arm opposite to the first end of the arm, the pulley shaft extending in parallel to the projection direction of the motor spindle;
a second cylinder pulley which is directly mounted on the pulley shaft to be rotatable around the pulley shaft;
a connecting member which attaches the first cylinder pulley to the second cylinder pulley;
a slider bearing which is directly secured to the second cylinder pulley;

a slider shaft which is slidably attached directly to the slider bearing, the slider shaft being attached directly to the ultrasonic element;
a roller shaft which is directly secured to the slider shaft;
a guide rail having an arced shape with a curvature center which is present on a line extending from the motor spindle in a direction away from the ultrasonic element; and
a roller which is directly mounted on the roller shaft, wherein the roller is configured to move along the guide rail while contacting the guide rail,
wherein when the motor drives the motor spindle to rotate, the rotation of the motor spindle is translated into rotational and telescopic movement of the slider shaft along the shape of the guide rail, whereby the ultrasonic element oscillates in accordance with the rotation of the motor spindle.

2. The ultrasonic probe according to claim 1, wherein an elastic member is located between the slider shaft and the slider bearing, so that the roller is pressed against a contacting face of the guide rail.

3. The ultrasonic probe according to claim 1, wherein a spring is arranged between the slider shaft and the slider bearing, so that the roller is pressed against a slider-bearing-side face of the guide rail.

4. The ultrasonic probe according to claim 1, further comprising an additional roller, wherein the plurality of rollers are arranged in contact with a slider-bearing-side face of the guide rail and a face thereof opposite the slider-bearing-side face, respectively, so as to sandwich the guide rail.

5. The ultrasonic probe according to claim 4, wherein:
the roller is rotatably attached to the slider shaft; and
the additional roller is provided so that the additional roller and the roller attached to the slider shaft are drawn near each other by a spring.

6. The ultrasonic probe according to claim 1, further comprising an additional guide rail,
wherein the plurality of guide rails sandwich the roller.

7. The ultrasonic probe according to claim 6, further comprising an additional roller, wherein the plurality of rollers are mounted and sandwiched between the guide rails, so that the rollers, impelled by springs, repel each other.

8. The ultrasonic probe according to claim 1, wherein:
a ratio of one to two is employed as a ratio of a diameter of the first cylinder pulley to a diameter of the second cylinder pulley; and
a length from the curvature center of the guide rail to a center of the motor spindle is set equal to a length from the center of the motor spindle to a center of the second cylinder pulley.

9. The ultrasonic probe according to claim 1, wherein a length of the arm extending from the first end to the second end, where the pulley shaft is secured, is set equal to or greater than a length extending from the pulley shaft to the roller shaft.

10. The ultrasonic probe according to claim 1, wherein:
the ultrasonic element that is secured to the slider shaft is an electronic-scanning, array-type ultrasonic element; and
when mechanical scanning is performed in a direction perpendicular to an electronic scanning direction of the array-type ultrasonic element, scanning of two cross sections perpendicular to each other is enabled by using both the electronic scanning and the mechanical scanning.

11. An ultrasonic probe comprising:
a probe casing;
a window which is provided on the probe casing, wherein an acoustic coupling fluid is enclosed in an area defined by the window and the probe casing;
an ultrasonic element which is arranged in the area defined by the window and the probe casing;
a motor which is secured to an outside of the probe casing, the motor including a motor spindle extending from the motor into the probe casing;
a first pulley which is secured to an inner wall of the probe casing, the first pulley having a through-hole, wherein the motor spindle of the motor penetrates the through-hole to project from the first pulley into an interior of the probe casing;
an arm which has a first end that is directly secured to the motor spindle that penetrates through and projects from the first pulley, wherein a longitudinal direction of the arm extends perpendicularly with respect to a projecting direction of the motor spindle;
a pulley shaft which is directly secured to a second end of the arm opposite to the first end of the arm, the pulley shaft extending in parallel to the projection direction of the motor spindle;
a second pulley which is directly mounted on the pulley shaft, the second pulley being rotatable around the pulley shaft;
a connecting member which attaches the first pulley to the second pulley;
a slider bearing which is directly secured to the second pulley;
a slider shaft which is slidably mounted directly to the slider bearing, wherein the ultrasonic element is secured directly to a first end of the slider shaft;
a roller shaft which is directly secured to a second end of the slider shaft;
a guide rail having an arced shape with a curvature center which is present on a line extending from the second end of the slider shaft in a direction toward the ultrasonic element, wherein the guide rail is attached to the probe casing; and
a roller which is directly mounted on the roller shaft that is connected to the slider shaft, wherein the roller is configured to move along the guide rail while contacting the guide rail,
wherein when the motor drives the motor spindle to rotate, the rotation of the motor spindle is translated into rotational and telescopic movement of the slider shaft along the shape of the guide rail, whereby the ultrasonic element oscillates in accordance with the rotation of the motor spindle.

12. The ultrasonic probe according to claim 11, wherein an elastic member is located between the slider shaft and the slider bearing, so that the roller is pressed against a contacting face of the guide rail.

13. The ultrasonic probe according to claim 12, wherein the elastic member comprises a spring which is arranged between the slider shaft and the slider bearing, so that the roller is kept in contact with a slider-bearing-side face of the guide rail.

14. The ultrasonic probe according to claim 12, the elastic member comprises a spring which is located between the slider shaft and the slider bearing, so that the spring brings the roller into contact with the guide rail on a side opposite the slider bearing.

15. The ultrasonic probe according to claim 11, further comprising an additional roller, wherein the plurality of rollers are arranged in contact with a slider-bearing-side face of the guide rail and a face thereof opposite the slider-bearing-side face, respectively, so as to sandwich the guide rail.

16. The ultrasonic probe according to claim 15, wherein:
the roller is rotatably attached to the slider shaft; and
the additional roller is provided so that the additional roller and the roller attached to the slider shaft are drawn near each other by a spring.

17. The ultrasonic probe according to claim 11, further comprising an additional guide rail, wherein the plurality of guide rails sandwich the roller.

18. The ultrasonic probe according to claim 17, further comprising an additional roller, wherein the plurality of rollers are mounted and sandwiched between the guide rails, so that the rollers, impelled by springs, repel each other.

19. The ultrasonic probe according to claim 11, wherein:
a ratio of one to two is employed as a ratio of a diameter of the first pulley to a diameter of the second pulley; and
a length of from the curvature center of the guide rail to the motor spindle is set equal to a length from a center of the motor spindle to a center of the second pulley.

20. The ultrasonic probe according to claim 11, wherein a length of the arm extending from the first end to the second end, where the pulley shaft is secured, is set equal to or greater than a length extending from the pulley shaft to the roller shaft.

21. The ultrasonic probe according to claim 11, wherein:
the ultrasonic element that is secured to the slider shaft is an electronic-scanning, array-type ultrasonic element; and
when mechanical scanning is performed in a direction perpendicular to an electronic scanning direction of the array-type ultrasonic element, scanning of two cross sections perpendicular to each other is enabled by using both the electronic scanning and the mechanical scanning.

22. An ultrasonic probe comprising:
a motor which has a rotary shaft;
a first arm which is directly fitted to a rotary shaft of the motor to be rotatable in accordance with a rotation of the rotary shaft, wherein the first arm has a longitudinal portion which is arranged perpendicularly to the rotary shaft of the motor and a distal end portion which extends perpendicularly from the longitudinal portion in parallel to the rotary shaft of the motor;
a second arm which is arranged parallel to the longitudinal portion of the first arm and which has a grooved portion extending longitudinally, wherein the distal end portion of the first arm is directly fitted on a groove engagement portion of the grooved portion of the second arm such that the distal end portion of the first arm is shiftable within the grooved portion in parallel to the second arm in accordance with rotation of the first arm;
an ultrasonic element which is directly attached to a distal end of the second arm;
a third arm which is arranged between the first arm and the second arm in parallel to the longitudinal portion of the first arm and to the second arm, wherein the third arm constitutes a linking mechanism having first and second rotatable ends;
a first shaft which is rotatably attached directly to the first rotatable end of the third arm and to a proximal end of the second arm opposite the distal end of the second arm to which the ultrasonic element is secured;
a second shaft which is rotatably attached directly to the second rotatable end of the third arm and to an intermediate portion of the longitudinal portion of the first arm at an arbitrary position between a rotational center of the first arm and the grooved portion of the second arm; and
a spring, for drawing an end portion, where the second arm and the third arm are connected, along a rotary-shaft perpendicular line, toward a side opposite the distal end of the second arm where the ultrasonic element is secured,
wherein the second arm, to which the ultrasonic element is attached, is oscillated in accordance with the rotation of the rotary shaft of the motor, and
wherein the ultrasonic element is rotated with a rotation radius that is longer than an actual distance relative to the rotary shaft.

23. The ultrasonic probe according to claim 22, wherein:
a length from a coupling point of the third arm that joins the first arm to a coupling point that joins the second arm is set equal to a length from a coupling point of the first arm that joins the third arm to a coupling point that joins the second arm;
the spring is arranged between an intersection point of the rotary-shaft perpendicular line with a trajectory of the distal end portion of the first arm, on a side opposite the end where the ultrasonic element is secured, and the end portion at which the second arm and the third arm are connected using the first shaft; and
a triangle formed using the individual coupling points is an isosceles triangle.

24. The ultrasonic probe according to claim 22, wherein the second shaft, which connects the first arm to the third arm, is located closer to a distal end side of the first arm from an intermediate point at a distance from the rotational center of the first arm to the distal end portion thereof.

25. The ultrasonic probe according to claim 22, further comprising:
a speed reduction mechanism which is provided for the rotary shaft of the motor; and
wherein the first arm is oscillated while the rotational center of the first arm is secured to the rotary shaft, a speed of which is reduced by the speed reduction mechanism.

26. The ultrasonic probe according to claim 22, wherein the ultrasonic element is an electronic scanning type element, and is to be mechanically oscillated in an electronic scanning direction and in a direction perpendicular to the electronic scanning direction.

27. An ultrasonic probe comprising:
a casing;
a window provided on the casing;
an ultrasonic element arranged in an area defined by the window and the casing;
a motor which has a rotary shaft;
a first arm which is directly fitted to a rotary shaft of the motor so to be rotatable in accordance with a rotation of the rotary shaft, wherein the first arm has a longitudinal portion which is arranged perpendicularly to the rotary shaft of the motor and a distal end portion which extends perpendicularly from the longitudinal portion in parallel to the rotary shaft of the motor;
a second arm, which is arranged parallel to the longitudinal portion of the first arm and which has a grooved portion extending longitudinally, wherein the distal end portion of the first arm is directly fitted on a groove engagement portion of the grooved portion of the second arm such that the distal end portion of the first arm is shiftable within the grooved portion in parallel to the second arm in accordance with rotation of the first arm, and wherein the ultrasonic element is directly attached to a window-side end of the second arm;
a third arm which is arranged between the first arm and the second arm in parallel to the longitudinal portion of the first arm and to the second arm, wherein the third arm constitutes a linking mechanism having first and second rotatable ends;
a first shaft which is rotatably attached directly to the first rotatable end of the third arm and to the second arm at a position between the window-side distal end where the ultrasonic element is mounted and the grooved portion;
a second shaft which is rotatably attached directly to the second rotatable end of the third arm and to an intermediate portion of the longitudinal portion of the first arm at an arbitrary position between a rotational center of the first arm and the grooved portion of the second arm; and
a spring for drawing an end portion where the second arm and the third arm are connected, along a rotary-shaft perpendicular line, toward the window-side end of the second arm where the ultrasonic element is secured,
wherein the second arm, to which the ultrasonic element is attached, is oscillated in accordance with the rotation of the rotary shaft of the motor, and
wherein a center of rotary motion of the ultrasonic element is in a vicinity of the window.

28. The ultrasonic probe according to claim 27, wherein:
a length from a coupling point of the third arm that joins the first arm to a coupling point that joins the second arm is set equal to a length from a coupling point of the first arm that joins the third arm to a coupling point that joins the second arm;
the spring is arranged between an intersection point of the rotary-shaft perpendicular line with a trajectory of the distal end portion of the first arm, on a side of the end where the ultrasonic element is secured, and the end portion at which the second arm and the third arm are connected using the first shaft; and
a triangle formed using the individual coupling points is an isosceles triangle.

29. The ultrasonic probe according to claim 27, wherein the second shaft, which connects the first arm to the third arm, is located near a distal end side of the first arm from an intermediate point at a distance from the rotational center of the first arm to the distal end portion thereof.

30. The ultrasonic probe according to claim 27, further comprising:
a speed reduction mechanism is provided for the rotary shaft of the motor;
wherein the rotational center of the first arm is secured to the rotary shaft, a speed of which is reduced by the speed reduction mechanism, and the motor is arranged separate from the window of the ultrasonic probe to perform oscillation.

31. The ultrasonic probe according to claim 27, wherein:
the ultrasonic element is an electronic scanning type element, and is to be mechanically oscillated in an electronic scanning direction and in a direction perpendicular to the electronic scanning direction.

32. The ultrasonic probe according to claim 27, wherein:
the ultrasonic element is a single element, which is to be independently rotated or oscillated to perform mechanical scanning, and is to be mechanically oscillated in a direction perpendicular to a direction for the mechanical scanning.

33. The ultrasonic probe according to claim 22, wherein:
the first shaft extends from the third arm in a direction normal to the third arm; and
the second shaft extends from the third arm in a direction opposite to the first shaft.

34. The ultrasonic probe according to claim 27, wherein:
the first shaft extends from the third arm in a direction normal to the third arm; and
the second shaft extends from the third arm in a direction opposite to the first shaft.

35. The ultrasonic probe according to claim 1, wherein the connecting member is attached to a part of the first cylinder pulley by a fastening device.

36. The ultrasonic probe according to claim 11, characterized in that the connecting member is attached to a part of the first pulley by a fastening device.

* * * * *